US012692525B1

(12) United States Patent
Ding et al.

(10) Patent No.: US 12,692,525 B1
(45) Date of Patent: Jul. 28, 2026

(54) THERMOSTABLE PURIFIED REVERSE TRANSCRIPTASE AND METHODS OF USE

(71) Applicants: Shaofeng Ding, Santa Fe Springs, CA (US); Qiang Liu, Rancho Cucamonga, CA (US)

(72) Inventors: Shaofeng Ding, Santa Fe Springs, CA (US); Qiang Liu, Rancho Cucamonga, CA (US)

( * ) Notice: Subject to any disclaimer, the term of this patent is extended or adjusted under 35 U.S.C. 154(b) by 846 days.

(21) Appl. No.: 17/541,254

(22) Filed: Dec. 3, 2021

Related U.S. Application Data

(60) Provisional application No. 63/124,055, filed on Dec. 11, 2020.

(51) Int. Cl.
*C12P 19/34* (2006.01)
*C12N 9/12* (2006.01)

(52) U.S. Cl.
CPC ............ *C12P 19/34* (2013.01); *C12N 9/1252* (2013.01); *C12Y 207/07007* (2013.01)

(58) Field of Classification Search
CPC ................... C12P 19/34; C12N 9/1252; C12Y 207/07007
See application file for complete search history.

(56) References Cited

U.S. PATENT DOCUMENTS

| | | | |
|---|---|---|---|
| 9,133,491 B2 * | 9/2015 | Ding | C12N 9/1252 |
| 9,926,543 B2 * | 3/2018 | Ding | C12Q 1/6844 |
| 2012/0258501 A1 * | 10/2012 | Bauer | C12N 9/1276 |
| | | | 435/91.51 |

FOREIGN PATENT DOCUMENTS

WO    WO-2008043765 A1 *  4/2008  ........... C12N 9/1252

OTHER PUBLICATIONS

Wacker et al. Analysis of One-Step and Two-Step Real-Time RT-PCR Using SuperScript III, 2005, Journal of Biomolecular Sciences, 16:266-271 (Year: 2005).*

* cited by examiner

*Primary Examiner* — Robert J Yamasaki
*Assistant Examiner* — Charles Zoltan Constantine

(57) ABSTRACT

Thermophilic purified Type A DNA-dependent DNA polymerases efficiently catalyze reverse transcription and RNA-dependent DNA pyrophosphorolysis using ribonucleic acid (RNA) templates, virtually also being reverse transcriptases. At optimal temperatures of 60° C. to 62° C., the thermophilic reverse transcriptases are particularly efficient for reverse transcription in RT-PCR and RT-PAP amplifications.

17 Claims, 3 Drawing Sheets

Specification includes a Sequence Listing.

A. Assay V with positive samples

B. Assay V with negative samples

C. Assay V with NTC samples

D. Assay VI with positive samples

E. Assay VI with negative samples

F. Assay VI with NTC samples

SEQUENCE LISTING

<160> NUMBER OF SEQ ID NOS: 28

<210> SEQ ID NO 1
<211> LENGTH: 831
<212> TYPE: PRT
<213> ORGANISM: Carboxydothermus pertinax

<400> SEQUENCE: 1

```
Met Gly Lys Val Val Leu Val Asp Gly Asn Ser Leu Leu His Arg Ala
1               5                   10                  15

Phe Phe Ala Leu Pro Pro Leu Lys Thr Ser Lys Gly Glu Pro Thr Gly
            20                  25                  30

Ala Val Tyr Gly Phe Leu Thr Met Leu Phe Lys Val Ile Lys Asp Glu
        35                  40                  45

Asn Pro Asp Tyr Leu Ala Val Ala Phe Asp Val Ser Arg Lys Thr Phe
    50                  55                  60

Arg Ser Asp Gln Phe Ser Ala Tyr Lys Gly His Arg Lys Glu Ala Pro
65                  70                  75                  80

Glu Glu Leu Val Pro Gln Phe Ala Leu Val Arg Glu Val Leu Lys Val
                85                  90                  95

Leu Asn Ile Pro Tyr Ile Glu Leu Met Gly Tyr Glu Ala Asp Asp Ile
            100                 105                 110

Ile Gly His Leu Ser Lys Val Phe Val Asn His Gly His Glu Val Lys
        115                 120                 125

Ile Tyr Thr Ala Asp Arg Asp Met Leu Gln Leu Val Glu Glu Lys Val
    130                 135                 140

Ala Val Tyr Leu Thr Lys Lys Gly Ile Thr Asp Leu Val Lys Met Asp
145                 150                 155                 160

Leu Ala Lys Val Gln Glu Asn Tyr Gly Leu Lys Pro Ile Gln Leu Ile
                165                 170                 175

Asp Val Lys Gly Leu Met Gly Asp Pro Ser Asp Asn Ile Pro Gly Val
            180                 185                 190
```

-continued

```
Pro Gly Ile Gly Glu Lys Thr Ala Leu Asp Leu Ile Lys Thr Tyr Gly
        195                 200                 205

Ser Leu Glu Glu Val Leu Thr His Lys Glu Glu Leu Lys Pro Lys Leu
        210                 215                 220

Lys Glu Lys Leu Thr Glu His Glu Asn Leu Ala Lys Ile Ser Lys Glu
225                 230                 235                 240

Leu Ala Thr Ile Leu Arg Glu Ile Pro Leu Glu Ile Ser Leu Glu Asp
                245                 250                 255

Leu Lys Val Lys Glu Pro Asp Tyr Glu Glu Ala Ala Lys Leu Phe Thr
                260                 265                 270

Arg Leu Glu Phe Lys Ser Phe Leu Lys Glu Val Glu Pro Lys Val Lys
                275                 280                 285

Lys Glu Tyr Gln Glu Ser Lys Glu Thr Val Asn Ile Glu Ile Ile Lys
        290                 295                 300

Ala Glu Gly Gln Val Val Val Phe Asn Asp Gly Phe Tyr Val Asp
305                 310                 315                 320

Asp Gly Glu Lys Thr Ser Phe Tyr Ser Leu Asp Gln Leu Val Asp Leu
                325                 330                 335

Gln Glu Ile Phe Arg Gly Lys Glu Ile Ile Thr Asp Asp Ala Lys Gly
                340                 345                 350

Ile Tyr Arg Phe Cys Leu Glu Lys Gly Ile Ser Phe Pro Lys Val Asn
                355                 360                 365

Phe Asp Ala Arg Ile Ala Ala Tyr Val Leu Asn Pro Ala Asp Gln Asn
        370                 375                 380

Pro Gly Leu Asn Gly Leu Tyr Ile Lys Tyr Asn Leu Pro Val Tyr Asp
385                 390                 395                 400

Asp Leu Phe Leu Asn Ile Arg Gly Leu Phe Tyr Leu Lys Lys Glu Met
                405                 410                 415

Leu Ala Lys Ile Arg Glu Gln Gln Glu Lys Leu Tyr Gln Glu Ile
                420                 425                 430

Glu Leu Pro Leu Thr Pro Val Leu Ala Arg Met Glu Phe Thr Gly Ile
                435                 440                 445

Gln Val Asp Arg Glu Ala Leu Lys Glu Met Ser Leu Glu Leu Gly Glu
        450                 455                 460

Gln Met Glu Ala Leu Thr Arg Glu Ile Tyr Ser Leu Ala Gly Glu Glu
465                 470                 475                 480

Phe Asn Leu Asn Ser Pro Lys Gln Leu Gly Val Ile Leu Phe Glu Lys
                485                 490                 495

Leu Gly Leu Pro Val Ile Lys Lys Thr Lys Thr Gly Tyr Ser Thr Asp
                500                 505                 510

Ala Glu Val Leu Glu Glu Leu Phe Ala Tyr His Glu Ile Val Gly Lys
        515                 520                 525

Ile Leu Asn Tyr Arg Gln Leu Met Lys Leu Lys Ser Thr Tyr Thr Asp
        530                 535                 540

Gly Leu Met Pro Leu Ile Asn Glu Tyr Thr Gly Lys Leu His Thr Thr
545                 550                 555                 560

Phe Asn Gln Thr Gly Thr Leu Thr Gly Arg Leu Ala Ser Ser Glu Pro
                565                 570                 575

Asn Leu Gln Asn Ile Pro Val Arg Leu Glu Leu Gly Arg Lys Leu Arg
                580                 585                 590

Lys Met Phe Ile Pro Ser Thr Gly Tyr Asp Tyr Ile Ile Ser Ala Asp
        595                 600                 605

Tyr Ser Gln Ile Glu Leu Arg Leu Leu Ala His Phe Ser Glu Glu Pro
```

```
            610             615             620
Lys Leu Ile Glu Ala Tyr Gln Lys Gly Glu Asp Ile His Arg Lys Thr
625             630             635             640

Ala Ala Glu Val Phe Gly Val Pro Leu Glu Glu Val Ser Leu Glu Met
                645             650             655

Arg Ser His Ala Lys Ser Val Asn Phe Gly Ile Val Tyr Gly Ile Ser
                660             665             670

Asp Phe Gly Leu Gly Arg Asp Leu Lys Ile Pro Arg Glu Val Ala Gly
            675             680             685

Lys Tyr Ile Lys Asn Tyr Phe Ala Asn Tyr Pro Lys Val Arg Glu Tyr
            690             695             700

Leu Asp Gly Leu Ile Arg Thr Ala Arg Glu Lys Gly Tyr Val Thr Thr
705             710             715             720

Leu Phe Gly Arg Arg Arg Tyr Ile Pro Glu Leu Thr Ala Lys Asn Arg
                725             730             735

Thr Val Gln Ser Phe Gly Glu Arg Thr Ala Met Asn Thr Pro Leu Gln
                740             745             750

Gly Thr Ala Ala Asp Ile Ile Lys Leu Ala Met Ile Asn Met Glu Arg
            755             760             765

Glu Leu Leu Arg Lys Gly Leu Lys Ser Arg Leu Leu Leu Ser Val His
            770             775             780

Asp Glu Leu Val Leu Glu Val Pro Ala Glu Glu Val Glu Glu Val Lys
785             790             795             800

Ser Leu Val Lys Lys Val Met Glu Ser Val Val Glu Leu Lys Val Pro
                805             810             815

Leu Ile Ala Glu Val Gly Met Gly Lys Asn Trp Tyr Glu Ala Lys
                820             825             830
```

<210> SEQ ID NO 2
<211> LENGTH: 831
<212> TYPE: PRT
<213> ORGANISM: Carboxydothermus ferrireducens

<400> SEQUENCE: 2

```
Met Gly Lys Val Val Leu Val Asp Gly Asn Ser Leu Leu His Arg Ala
1               5               10              15

Phe Phe Ala Leu Pro Pro Leu Lys Thr Thr Lys Gly Glu Pro Thr Gly
                20              25              30

Ala Val Tyr Gly Phe Leu Thr Met Leu Phe Arg Val Ile Lys Asp Glu
            35              40              45

Lys Pro Glu Tyr Leu Ala Val Ala Phe Asp Val Ser Arg Lys Thr Phe
            50              55              60

Arg Thr Lys Gln Phe Thr Ala Tyr Lys Gly His Arg Lys Glu Ala Pro
65              70              75              80

Asp Glu Leu Val Pro Gln Phe Ala Leu Val Arg Glu Val Leu Lys Val
                85              90              95

Leu Asn Val Pro Tyr Ile Glu Leu Asp Gly Tyr Glu Ala Asp Asp Ile
                100             105             110

Ile Gly His Leu Ser Arg Val Phe Ala Gly Gln Gly His Glu Val Val
            115             120             125

Ile Tyr Thr Ala Asp Arg Asp Met Leu Gln Leu Val Asp Glu Lys Thr
            130             135             140

Val Val Tyr Leu Thr Lys Lys Gly Ile Thr Glu Leu Val Lys Met Asp
145             150             155             160
```

```
Leu Ala Ala Ile Leu Glu Ser Tyr Gly Leu Lys Pro Lys Gln Leu Val
                165                 170                 175

Asp Val Lys Gly Leu Met Gly Asp Pro Ser Asp Asn Ile Pro Gly Val
                180                 185                 190

Pro Gly Ile Gly Glu Lys Thr Ala Leu Asp Leu Ile Lys Thr Tyr Gly
                195                 200                 205

Ser Val Glu Glu Val Leu Ala His Lys Asp Glu Leu Lys Pro Lys Leu
        210                 215                 220

Arg Glu Lys Leu Ala Glu His Glu Asn Leu Ala Lys Ile Ser Lys Gln
225                 230                 235                 240

Leu Ala Thr Ile Leu Arg Glu Ile Pro Leu Glu Ile Ser Leu Glu Asp
                245                 250                 255

Leu Lys Val Lys Glu Pro Asn Tyr Glu Glu Val Ala Lys Leu Phe Leu
                260                 265                 270

Arg Leu Glu Phe Lys Ser Phe Leu Lys Glu Ile Glu Pro Lys Ile Lys
        275                 280                 285

Lys Glu Tyr Gln Glu Gly Lys Asp Leu Val Gln Phe Glu Thr Val Glu
        290                 295                 300

Thr Glu Gly Gln Ile Ala Val Val Phe Ser Asp Gly Phe Tyr Val Asp
305                 310                 315                 320

Asp Gly Glu Lys Thr Lys Phe Tyr Ser Leu Asp Arg Leu Asn Glu Ile
                325                 330                 335

Gln Glu Ile Phe Arg Asn Lys Lys Ile Ile Thr Asp Asp Ala Lys Gly
                340                 345                 350

Ile Tyr His Val Cys Leu Glu Lys Gly Leu Thr Phe Pro Glu Val Cys
        355                 360                 365

Phe Asp Ala Arg Ile Ala Ala Tyr Val Leu Asn Pro Ala Asp Gln Asn
        370                 375                 380

Pro Gly Leu Lys Gly Leu Tyr Leu Lys Tyr Asp Leu Pro Val Tyr Glu
385                 390                 395                 400

Asp Val Ser Leu Asn Ile Arg Gly Leu Phe Tyr Leu Lys Lys Glu Met
                405                 410                 415

Met Lys Lys Ile Phe Glu Gln Glu Gln Glu Arg Leu Phe Tyr Glu Ile
                420                 425                 430

Glu Leu Pro Leu Thr Pro Val Leu Ala Gln Met Glu His Thr Gly Ile
        435                 440                 445

Gln Val Asp Arg Glu Ala Leu Lys Glu Met Ser Leu Glu Leu Gly Glu
        450                 455                 460

Gln Ile Glu Glu Leu Ile Arg Glu Ile Tyr Ala Leu Ala Gly Glu Glu
465                 470                 475                 480

Phe Asn Leu Asn Ser Pro Lys Gln Leu Gly Val Ile Leu Phe Glu Lys
                485                 490                 495

Leu Gly Leu Pro Val Ile Lys Lys Thr Lys Thr Gly Tyr Ser Thr Asp
                500                 505                 510

Ala Glu Val Leu Glu Glu Leu Leu Pro Tyr His Glu Ile Ile Gly Lys
        515                 520                 525

Ile Leu Asn Tyr Arg Gln Leu Met Lys Leu Lys Ser Thr Tyr Thr Asp
        530                 535                 540

Gly Leu Met Pro Leu Ile Asn Glu Arg Thr Gly Lys Leu His Thr Thr
545                 550                 555                 560

Phe Asn Gln Thr Gly Thr Leu Thr Gly Arg Leu Ala Ser Ser Glu Pro
                565                 570                 575

Asn Leu Gln Asn Ile Pro Ile Arg Leu Glu Leu Gly Arg Lys Leu Arg
```

-continued

```
            580                 585                 590

Lys Met Phe Ile Pro Ser Pro Gly Tyr Asp Tyr Ile Val Ser Ala Asp
        595                 600                 605

Tyr Ser Gln Ile Glu Leu Arg Leu Leu Ala His Phe Ser Glu Glu Pro
        610             615             620

Lys Leu Ile Glu Ala Tyr Gln Lys Gly Glu Asp Ile His Arg Lys Thr
625                 630             635                 640

Ala Ser Glu Val Phe Gly Val Ser Leu Glu Glu Val Thr Pro Glu Met
                645             650                 655

Arg Ala His Ala Lys Ser Val Asn Phe Gly Ile Val Tyr Gly Ile Ser
            660             665             670

Asp Phe Gly Leu Gly Arg Asp Leu Lys Ile Pro Arg Glu Val Ala Gly
        675             680             685

Lys Tyr Ile Lys Asn Tyr Phe Ala Asn Tyr Pro Lys Val Arg Glu Tyr
        690             695             700

Leu Asp Glu Leu Val Arg Thr Ala Arg Glu Lys Gly Tyr Val Thr Thr
705             710             715                 720

Leu Phe Gly Arg Arg Arg Tyr Ile Pro Glu Leu Ser Ser Lys Asn Arg
                725             730                 735

Thr Val Gln Gly Phe Gly Glu Arg Thr Ala Met Asn Thr Pro Leu Gln
            740             745             750

Gly Ser Ala Ala Asp Ile Ile Lys Leu Ala Met Ile Asn Val Glu Lys
            755             760             765

Glu Leu Lys Ala Arg Lys Leu Lys Ser Arg Leu Leu Leu Ser Val His
        770             775             780

Asp Glu Leu Val Leu Glu Val Pro Ala Glu Glu Leu Glu Glu Val Lys
785             790             795                 800

Ala Leu Val Lys Gly Val Met Glu Ser Val Val Glu Leu Lys Val Pro
            805             810             815

Leu Ile Ala Glu Val Gly Ala Gly Lys Asn Trp Tyr Glu Ala Lys
            820             825             830
```

<210> SEQ ID NO 3
<211> LENGTH: 831
<212> TYPE: PRT
<213> ORGANISM: Carboxydothermus islandicus
<400> SEQUENCE: 3

```
Met Gly Lys Val Val Leu Val Asp Gly Asn Ser Leu Leu His Arg Ala
1               5                   10                  15

Phe Phe Ala Leu Pro Pro Leu Lys Thr Thr Lys Gly Glu Pro Thr Gly
            20                  25                  30

Ala Val Tyr Gly Phe Leu Thr Met Leu Phe Arg Val Ile Arg Asp Glu
            35                  40                  45

Lys Pro Glu Tyr Leu Ala Val Ala Phe Asp Val Ser Arg Lys Thr Phe
        50                  55                  60

Arg Thr Glu Gln Phe Thr Ala Tyr Lys Gly His Arg Lys Glu Ala Pro
65                  70                  75                  80

Asp Glu Leu Val Pro Gln Phe Ala Leu Val Arg Glu Val Leu Lys Val
                85                  90                  95

Leu Asn Val Pro Tyr Ile Glu Leu Asp Gly Tyr Glu Ala Asp Asp Ile
            100                 105                 110

Ile Gly His Leu Ser Arg Val Phe Ala Gly Gln Gly His Glu Val Val
            115                 120                 125
```

Ile Tyr Thr Ala Asp Arg Asp Met Leu Gln Leu Val Asp Glu Lys Thr
    130                 135                 140

Val Val Tyr Leu Thr Lys Lys Gly Ile Thr Glu Leu Val Lys Met Asp
145                 150                 155                 160

Leu Ala Glu Val Leu Glu Asn Tyr Gly Leu Lys Pro Gln Gln Leu Val
                165                 170                 175

Asp Val Lys Gly Leu Met Gly Asp Pro Ser Asp Asn Ile Pro Gly Val
                180                 185                 190

Pro Gly Ile Gly Glu Lys Thr Ala Leu Asp Leu Ile Lys Thr Tyr Gly
                195                 200                 205

Ser Val Glu Glu Val Leu Ala Arg Lys Glu Glu Leu Lys Pro Lys Leu
    210                 215                 220

Arg Glu Lys Leu Ala Glu His Glu Ser Leu Ala Lys Ile Ser Lys Gln
225                 230                 235                 240

Leu Ala Thr Ile Leu Arg Glu Ile Pro Leu Glu Ile Ser Leu Glu Asp
                245                 250                 255

Leu Lys Val Lys Glu Pro Asn Tyr Glu Glu Val Ala Lys Leu Phe Leu
                260                 265                 270

Arg Leu Glu Phe Lys Ser Phe Leu Lys Glu Ile Glu Pro Lys Ile Lys
    275                 280                 285

Asn Glu Tyr Gln Glu Ser Lys Glu Leu Val Gln Phe Glu Pro Val Ala
    290                 295                 300

Thr Glu Glu Arg Ile Ala Val Ile Phe Asn Asn Gly Phe Tyr Val Asp
305                 310                 315                 320

Asp Gly Glu Lys Thr Lys Phe Tyr Ser Leu Glu Gln Leu Phe Glu Ile
                325                 330                 335

Gln Glu Ile Phe Arg Asn Lys Lys Ile Ile Thr Asp Asp Ala Lys Gly
                340                 345                 350

Ile Tyr His Val Cys Leu Glu Lys Gly Leu Thr Phe Pro Glu Ile Cys
    355                 360                 365

Phe Asp Ala Arg Ile Ala Ala Tyr Val Leu Asn Pro Ala Asp Gln Asn
    370                 375                 380

Pro Gly Leu Lys Gly Leu Tyr Leu Lys Tyr Gly Leu Pro Val Phe Glu
385                 390                 395                 400

Asp Phe Ser Leu Asn Ile Arg Gly Leu Phe Tyr Leu Trp Lys Glu Met
                405                 410                 415

Met Glu Lys Val His Glu Gln Glu Gln Glu Arg Leu Phe Tyr Glu Ile
                420                 425                 430

Glu Leu Pro Leu Thr Pro Val Leu Ala Gln Met Glu His Thr Gly Ile
                435                 440                 445

Gln Val Asp Arg Glu Ala Leu Lys Glu Met Ser Val Glu Leu Gly Glu
    450                 455                 460

Gln Ile Glu Glu Leu Ile Arg Glu Ile Tyr Ala Leu Ala Gly Glu Glu
465                 470                 475                 480

Phe Asn Leu Asn Ser Pro Arg Gln Leu Gly Val Ile Leu Phe Glu Lys
                485                 490                 495

Leu Gly Leu Pro Val Ile Lys Lys Thr Lys Thr Gly Tyr Ser Thr Asp
                500                 505                 510

Ala Glu Val Leu Glu Glu Leu Leu Pro Tyr His Glu Ile Ile Gly Lys
                515                 520                 525

Ile Leu Thr Tyr Arg Gln Leu Met Lys Leu Lys Ser Thr Tyr Thr Asp
    530                 535                 540

Gly Leu Met Pro Leu Ile Asn Glu Arg Thr Gly Lys Leu His Thr Thr

-continued

```
545                     550                     555                     560

Phe Asn Gln Thr Gly Thr Leu Thr Gly Arg Leu Ala Ser Ser Glu Pro
            565                     570                     575

Asn Leu Gln Asn Ile Pro Val Arg Leu Glu Leu Gly Arg Lys Leu Arg
            580                     585                     590

Lys Met Phe Ile Pro Ser Pro Gly Tyr Asp Tyr Ile Val Ser Ala Asp
            595                     600                     605

Tyr Ser Gln Ile Glu Leu Arg Leu Leu Ala His Phe Ser Glu Glu Pro
            610                     615                     620

Lys Leu Ile Glu Ala Tyr Gln Lys Gly Glu Asp Ile His Arg Lys Thr
625                     630                     635                     640

Ala Ser Glu Val Phe Gly Val Pro Leu Glu Glu Val Thr Pro Glu Met
            645                     650                     655

Arg Ala His Ala Lys Ser Val Asn Phe Gly Ile Val Tyr Gly Ile Ser
            660                     665                     670

Asp Phe Gly Leu Gly Arg Asp Leu Lys Ile Pro Arg Glu Ile Ala Gly
            675                     680                     685

Lys Tyr Ile Lys Asn Tyr Phe Thr Asn Tyr Pro Arg Val Arg Glu Tyr
            690                     695                     700

Leu Asp Glu Leu Val Arg Thr Ala Arg Glu Lys Gly Tyr Val Thr Thr
705                     710                     715                     720

Leu Phe Gly Arg Arg Arg Tyr Ile Pro Glu Leu Ser Ser Lys Asn Arg
            725                     730                     735

Thr Val Gln Gly Phe Gly Glu Arg Thr Ala Met Asn Thr Pro Leu Gln
            740                     745                     750

Gly Ser Ala Ala Asp Ile Ile Lys Leu Ala Met Ile Asn Val Glu Arg
            755                     760                     765

Glu Leu Lys Asn Ser Lys Leu Arg Ser Arg Leu Leu Leu Ser Val His
            770                     775                     780

Asp Glu Leu Val Leu Glu Val Pro Ala Glu Glu Leu Glu Glu Val Lys
785                     790                     795                     800

Gly Leu Val Lys Gly Val Met Glu Ser Val Val Glu Leu Lys Val Pro
            805                     810                     815

Leu Ile Ala Glu Val Gly Ala Gly Lys Asn Trp Tyr Glu Ala Lys
            820                     825                     830

<210> SEQ ID NO 4
<211> LENGTH: 586
<212> TYPE: PRT
<213> ORGANISM: Carboxydothermus pertinax

<400> SEQUENCE: 4

Met Gly Ile Pro Leu Glu Ile Ser Leu Glu Asp Leu Lys Val Lys Glu
1                   5                   10                  15

Pro Asp Tyr Glu Glu Ala Ala Lys Leu Phe Thr Arg Leu Glu Phe Lys
            20                  25                  30

Ser Phe Leu Lys Glu Val Glu Pro Lys Val Lys Lys Glu Tyr Gln Glu
            35                  40                  45

Ser Lys Glu Thr Val Asn Ile Glu Ile Ile Lys Ala Glu Gly Gln Val
            50                  55                  60

Val Val Val Phe Asn Asp Gly Phe Tyr Val Asp Asp Gly Glu Lys Thr
65                  70                  75                  80

Ser Phe Tyr Ser Leu Asp Gln Leu Val Asp Leu Gln Glu Ile Phe Arg
            85                  90                  95
```

-continued

```
Gly Lys Glu Ile Ile Thr Asp Asp Ala Lys Gly Ile Tyr Arg Phe Cys
            100                 105                 110

Leu Glu Lys Gly Ile Ser Phe Pro Lys Val Asn Phe Asp Ala Arg Ile
            115                 120                 125

Ala Ala Tyr Val Leu Asn Pro Ala Asp Gln Asn Pro Gly Leu Asn Gly
            130                 135                 140

Leu Tyr Ile Lys Tyr Asn Leu Pro Val Tyr Asp Asp Leu Phe Leu Asn
145                 150                 155                 160

Ile Arg Gly Leu Phe Tyr Leu Lys Lys Glu Met Leu Ala Lys Ile Arg
                165                 170                 175

Glu Gln Gln Gln Glu Lys Leu Tyr Gln Glu Ile Glu Leu Pro Leu Thr
            180                 185                 190

Pro Val Leu Ala Arg Met Glu Phe Thr Gly Ile Gln Val Asp Arg Glu
            195                 200                 205

Ala Leu Lys Glu Met Ser Leu Glu Leu Gly Glu Gln Met Glu Ala Leu
            210                 215                 220

Thr Arg Glu Ile Tyr Ser Leu Ala Gly Glu Glu Phe Asn Leu Asn Ser
225                 230                 235                 240

Pro Lys Gln Leu Gly Val Ile Leu Phe Glu Lys Leu Gly Leu Pro Val
                245                 250                 255

Ile Lys Lys Thr Lys Thr Gly Tyr Ser Thr Asp Ala Glu Val Leu Glu
            260                 265                 270

Glu Leu Phe Ala Tyr His Glu Ile Val Gly Lys Ile Leu Asn Tyr Arg
            275                 280                 285

Gln Leu Met Lys Leu Lys Ser Thr Tyr Thr Asp Gly Leu Met Pro Leu
            290                 295                 300

Ile Asn Glu Tyr Thr Gly Lys Leu His Thr Thr Phe Asn Gln Thr Gly
305                 310                 315                 320

Thr Leu Thr Gly Arg Leu Ala Ser Ser Glu Pro Asn Leu Gln Asn Ile
                325                 330                 335

Pro Val Arg Leu Glu Leu Gly Arg Lys Leu Arg Lys Met Phe Ile Pro
            340                 345                 350

Ser Thr Gly Tyr Asp Tyr Ile Ile Ser Ala Asp Tyr Ser Gln Ile Glu
            355                 360                 365

Leu Arg Leu Leu Ala His Phe Ser Glu Glu Pro Lys Leu Ile Glu Ala
            370                 375                 380

Tyr Gln Lys Gly Glu Asp Ile His Arg Lys Thr Ala Ala Glu Val Phe
385                 390                 395                 400

Gly Val Pro Leu Glu Glu Val Ser Leu Glu Met Arg Ser His Ala Lys
                405                 410                 415

Ser Val Asn Phe Gly Ile Val Tyr Gly Ile Ser Asp Phe Gly Leu Gly
            420                 425                 430

Arg Asp Leu Lys Ile Pro Arg Glu Val Ala Gly Lys Tyr Ile Lys Asn
            435                 440                 445

Tyr Phe Ala Asn Tyr Pro Lys Val Arg Glu Tyr Leu Asp Gly Leu Ile
            450                 455                 460

Arg Thr Ala Arg Glu Lys Gly Tyr Val Thr Thr Leu Phe Gly Arg Arg
465                 470                 475                 480

Arg Tyr Ile Pro Glu Leu Thr Ala Lys Asn Arg Thr Val Gln Ser Phe
                485                 490                 495

Gly Glu Arg Thr Ala Met Asn Thr Pro Leu Gln Gly Thr Ala Ala Asp
            500                 505                 510

Ile Ile Lys Leu Ala Met Ile Asn Met Glu Arg Glu Leu Leu Arg Lys
```

-continued

---

```
                515                 520                 525

Gly Leu Lys Ser Arg Leu Leu Leu Ser Val His Asp Glu Leu Val Leu
        530                 535                 540

Glu Val Pro Ala Glu Glu Val Glu Glu Val Lys Ser Leu Val Lys Lys
545                 550                 555                 560

Val Met Glu Ser Val Val Glu Leu Lys Val Pro Leu Ile Ala Glu Val
                565                 570                 575

Gly Met Gly Lys Asn Trp Tyr Glu Ala Lys
            580                 585

<210> SEQ ID NO 5
<211> LENGTH: 831
<212> TYPE: PRT
<213> ORGANISM: Carboxydothermus pertinax

<400> SEQUENCE: 5

Met Gly Lys Val Val Leu Val Asp Gly Asn Ser Leu Leu His Arg Ala
1               5                   10                  15

Phe Phe Ala Leu Pro Pro Leu Lys Thr Ser Lys Gly Glu Pro Thr Gly
                20                  25                  30

Ala Val Tyr Gly Phe Leu Thr Met Leu Phe Lys Val Ile Lys Asp Glu
            35                  40                  45

Asn Pro Asp Tyr Leu Ala Val Ala Phe Asp Val Ser Arg Lys Thr Phe
        50                  55                  60

Arg Ser Asp Gln Phe Ser Ala Tyr Lys Gly His Arg Lys Glu Ala Pro
65                  70                  75                  80

Glu Glu Leu Val Pro Gln Phe Ala Leu Val Arg Glu Val Leu Lys Val
                85                  90                  95

Leu Asn Ile Pro Tyr Ile Glu Leu Met Gly Tyr Glu Ala Asp Asp Ile
            100                 105                 110

Ile Gly His Leu Ser Lys Val Phe Val Asn His Gly His Glu Val Lys
        115                 120                 125

Ile Tyr Thr Ala Asp Arg Asp Met Leu Gln Leu Val Glu Glu Lys Val
        130                 135                 140

Ala Val Tyr Leu Thr Lys Lys Gly Ile Thr Asp Leu Val Lys Met Asp
145                 150                 155                 160

Leu Ala Lys Val Gln Glu Asn Tyr Gly Leu Lys Pro Ile Gln Leu Ile
                165                 170                 175

Asp Val Lys Gly Leu Met Gly Asp Pro Ser Asp Asn Ile Pro Gly Val
            180                 185                 190

Pro Gly Ile Gly Glu Lys Thr Ala Leu Asp Leu Ile Lys Thr Tyr Gly
        195                 200                 205

Ser Leu Glu Glu Val Leu Thr His Lys Glu Glu Leu Lys Pro Lys Leu
        210                 215                 220

Lys Glu Lys Leu Thr Glu His Glu Asn Leu Ala Lys Ile Ser Lys Glu
225                 230                 235                 240

Leu Ala Thr Ile Leu Arg Glu Ile Pro Leu Glu Ile Ser Leu Glu Asp
                245                 250                 255

Leu Lys Val Lys Glu Pro Asp Tyr Glu Glu Ala Ala Lys Leu Phe Thr
            260                 265                 270

Arg Leu Glu Phe Lys Ser Phe Leu Lys Glu Val Glu Pro Lys Val Lys
        275                 280                 285

Lys Glu Tyr Gln Glu Ser Lys Glu Thr Val Asn Ile Glu Ile Ile Lys
        290                 295                 300
```

-continued

```
Ala Glu Gly Gln Val Val Val Val Phe Asn Asp Gly Phe Tyr Val Asp
305             310                 315                 320

Asp Gly Glu Lys Thr Ser Phe Tyr Ser Leu Asp Gln Leu Val Asp Leu
                325             330                 335

Gln Glu Ile Phe Arg Gly Lys Glu Ile Ile Thr Asp Asp Ala Lys Gly
            340             345             350

Ile Tyr Arg Phe Cys Leu Glu Lys Gly Ile Ser Phe Pro Lys Val Asn
            355             360             365

Phe Asp Ala Arg Ile Ala Ala Tyr Val Leu Asn Pro Ala Asp Gln Asn
    370             375             380

Pro Gly Leu Asn Gly Leu Tyr Ile Lys Tyr Asn Leu Pro Val Tyr Asp
385             390             395                 400

Asp Leu Phe Leu Asn Ile Arg Gly Leu Phe Tyr Leu Lys Lys Glu Met
            405             410             415

Leu Ala Lys Ile Arg Glu Gln Gln Gln Glu Lys Leu Tyr Gln Glu Ile
            420             425             430

Glu Leu Pro Leu Thr Pro Val Leu Ala Arg Met Glu Phe Thr Gly Ile
            435             440             445

Gln Val Asp Arg Glu Ala Leu Lys Glu Met Ser Leu Glu Leu Gly Glu
    450             455             460

Gln Met Glu Ala Leu Thr Arg Glu Ile Tyr Ser Leu Ala Gly Glu Glu
465             470             475                 480

Phe Asn Leu Asn Ser Pro Lys Gln Leu Gly Val Ile Leu Phe Glu Lys
            485             490             495

Leu Gly Leu Pro Val Ile Lys Lys Thr Lys Thr Gly Tyr Ser Thr Asp
            500             505             510

Ala Glu Val Leu Glu Glu Leu Phe Ala Tyr His Glu Ile Val Gly Lys
            515             520             525

Ile Leu Asn Tyr Arg Gln Leu Met Lys Leu Lys Ser Thr Tyr Thr Asp
    530             535             540

Gly Leu Met Pro Leu Ile Asn Glu Tyr Thr Gly Lys Leu His Thr Thr
545             550             555                 560

Phe Asn Gln Thr Gly Thr Leu Thr Gly Arg Leu Ala Ser Ser Glu Pro
            565             570             575

Asn Leu Gln Asn Ile Pro Val Arg Leu Glu Leu Gly Arg Lys Leu Arg
            580             585             590

Lys Met Phe Ile Pro Ser Thr Gly Tyr Asp Tyr Ile Ile Ser Ala Asp
            595             600             605

Tyr Ser Gln Ile Glu Leu Arg Leu Leu Ala His Phe Ser Glu Glu Pro
    610             615             620

Lys Leu Ile Glu Ala Tyr Gln Lys Gly Glu Asp Ile His Arg Lys Thr
625             630             635                 640

Ala Ala Glu Val Phe Gly Val Pro Leu Glu Glu Val Ser Leu Glu Met
            645             650             655

Arg Ser His Ala Lys Ser Val Asn Tyr Gly Ile Val Tyr Gly Ile Ser
            660             665             670

Asp Phe Gly Leu Gly Arg Asp Leu Lys Ile Pro Arg Glu Val Ala Gly
            675             680             685

Lys Tyr Ile Lys Asn Tyr Phe Ala Asn Tyr Pro Lys Val Arg Glu Tyr
            690             695             700

Leu Asp Gly Leu Ile Arg Thr Ala Arg Glu Lys Gly Tyr Val Thr Thr
705             710             715                 720

Leu Phe Gly Arg Arg Arg Tyr Ile Pro Glu Leu Thr Ala Lys Asn Arg
```

43

44

```
                    725                 730                 735

Thr Val Gln Ser Phe Gly Glu Arg Thr Ala Met Asn Thr Pro Leu Gln
                740                 745                 750

Gly Thr Ala Ala Asp Ile Ile Lys Leu Ala Met Ile Asn Met Glu Arg
            755                 760                 765

Glu Leu Leu Arg Lys Gly Leu Lys Ser Arg Leu Leu Leu Ser Val His
    770                 775                 780

Asp Glu Leu Val Leu Glu Val Pro Ala Glu Glu Val Glu Glu Val Lys
785                 790                 795                 800

Ser Leu Val Lys Lys Val Met Glu Ser Val Val Glu Leu Lys Val Pro
                805                 810                 815

Leu Ile Ala Glu Val Gly Met Gly Lys Asn Trp Tyr Glu Ala Lys
            820                 825                 830

<210> SEQ ID NO 6
<211> LENGTH: 831
<212> TYPE: PRT
<213> ORGANISM: Carboxydothermus ferrireducens

<400> SEQUENCE: 6

Met Gly Lys Val Val Leu Val Asp Gly Asn Ser Leu Leu His Arg Ala
1               5                   10                  15

Phe Phe Ala Leu Pro Pro Leu Lys Thr Thr Lys Gly Glu Pro Thr Gly
                20                  25                  30

Ala Val Tyr Gly Phe Leu Thr Met Leu Phe Arg Val Ile Lys Asp Glu
            35                  40                  45

Lys Pro Glu Tyr Leu Ala Val Ala Phe Asp Val Ser Arg Lys Thr Phe
    50                  55                  60

Arg Thr Lys Gln Phe Thr Ala Tyr Lys Gly His Arg Lys Glu Ala Pro
65                  70                  75                  80

Asp Glu Leu Val Pro Gln Phe Ala Leu Val Arg Glu Val Leu Lys Val
                85                  90                  95

Leu Asn Val Pro Tyr Ile Glu Leu Asp Gly Tyr Glu Ala Asp Asp Ile
            100                 105                 110

Ile Gly His Leu Ser Arg Val Phe Ala Gly Gln Gly His Glu Val Val
            115                 120                 125

Ile Tyr Thr Ala Asp Arg Asp Met Leu Gln Leu Val Asp Glu Lys Thr
    130                 135                 140

Val Val Tyr Leu Thr Lys Lys Gly Ile Thr Glu Leu Val Lys Met Asp
145                 150                 155                 160

Leu Ala Ala Ile Leu Glu Ser Tyr Gly Leu Lys Pro Lys Gln Leu Val
                165                 170                 175

Asp Val Lys Gly Leu Met Gly Asp Pro Ser Asp Asn Ile Pro Gly Val
            180                 185                 190

Pro Gly Ile Gly Glu Lys Thr Ala Leu Asp Leu Ile Lys Thr Tyr Gly
        195                 200                 205

Ser Val Glu Glu Val Leu Ala His Lys Asp Glu Leu Lys Pro Lys Leu
    210                 215                 220

Arg Glu Lys Leu Ala Glu His Glu Asn Leu Ala Lys Ile Ser Lys Gln
225                 230                 235                 240

Leu Ala Thr Ile Leu Arg Glu Ile Pro Leu Glu Ile Ser Leu Glu Asp
                245                 250                 255

Leu Lys Val Lys Glu Pro Asn Tyr Glu Glu Val Ala Lys Leu Phe Leu
            260                 265                 270
```

-continued

```
Arg Leu Glu Phe Lys Ser Phe Leu Lys Glu Ile Glu Pro Lys Ile Lys
        275                 280                 285

Lys Glu Tyr Gln Glu Gly Lys Asp Leu Val Gln Phe Glu Thr Val Glu
        290                 295                 300

Thr Glu Gly Gln Ile Ala Val Val Phe Ser Asp Gly Phe Tyr Val Asp
305                 310                 315                 320

Asp Gly Glu Lys Thr Lys Phe Tyr Ser Leu Asp Arg Leu Asn Glu Ile
                325                 330                 335

Gln Glu Ile Phe Arg Asn Lys Lys Ile Ile Thr Asp Asp Ala Lys Gly
                340                 345                 350

Ile Tyr His Val Cys Leu Glu Lys Gly Leu Thr Phe Pro Glu Val Cys
            355                 360                 365

Phe Asp Ala Arg Ile Ala Ala Tyr Val Leu Asn Pro Ala Asp Gln Asn
        370                 375                 380

Pro Gly Leu Lys Gly Leu Tyr Leu Lys Tyr Asp Leu Pro Val Tyr Glu
385                 390                 395                 400

Asp Val Ser Leu Asn Ile Arg Gly Leu Phe Tyr Leu Lys Lys Glu Met
                405                 410                 415

Met Lys Lys Ile Phe Glu Gln Glu Gln Glu Arg Leu Phe Tyr Glu Ile
                420                 425                 430

Glu Leu Pro Leu Thr Pro Val Leu Ala Gln Met Glu His Thr Gly Ile
            435                 440                 445

Gln Val Asp Arg Glu Ala Leu Lys Glu Met Ser Leu Glu Leu Gly Glu
        450                 455                 460

Gln Ile Glu Glu Leu Ile Arg Glu Ile Tyr Ala Leu Ala Gly Glu Glu
465                 470                 475                 480

Phe Asn Leu Asn Ser Pro Lys Gln Leu Gly Val Ile Leu Phe Glu Lys
                485                 490                 495

Leu Gly Leu Pro Val Ile Lys Lys Thr Lys Thr Gly Tyr Ser Thr Asp
            500                 505                 510

Ala Glu Val Leu Glu Glu Leu Leu Pro Tyr His Glu Ile Ile Gly Lys
        515                 520                 525

Ile Leu Asn Tyr Arg Gln Leu Met Lys Leu Lys Ser Thr Tyr Thr Asp
        530                 535                 540

Gly Leu Met Pro Leu Ile Asn Glu Arg Thr Gly Lys Leu His Thr Thr
545                 550                 555                 560

Phe Asn Gln Thr Gly Thr Leu Thr Gly Arg Leu Ala Ser Ser Glu Pro
                565                 570                 575

Asn Leu Gln Asn Ile Pro Ile Arg Leu Glu Leu Gly Arg Lys Leu Arg
            580                 585                 590

Lys Met Phe Ile Pro Ser Pro Gly Tyr Asp Tyr Ile Val Ser Ala Asp
        595                 600                 605

Tyr Ser Gln Ile Glu Leu Arg Leu Leu Ala His Phe Ser Glu Glu Pro
        610                 615                 620

Lys Leu Ile Glu Ala Tyr Gln Lys Gly Glu Asp Ile His Arg Lys Thr
625                 630                 635                 640

Ala Ser Glu Val Phe Gly Val Ser Leu Glu Glu Val Thr Pro Glu Met
                645                 650                 655

Arg Ala His Ala Lys Ser Val Asn Tyr Gly Ile Val Tyr Gly Ile Ser
            660                 665                 670

Asp Phe Gly Leu Gly Arg Asp Leu Lys Ile Pro Arg Glu Val Ala Gly
        675                 680                 685

Lys Tyr Ile Lys Asn Tyr Phe Ala Asn Tyr Pro Lys Val Arg Glu Tyr
```

-continued

```
     690              695              700

Leu Asp Glu Leu Val Arg Thr Ala Arg Glu Lys Gly Tyr Val Thr Thr
705              710              715              720

Leu Phe Gly Arg Arg Arg Tyr Ile Pro Glu Leu Ser Ser Lys Asn Arg
             725              730              735

Thr Val Gln Gly Phe Gly Glu Arg Thr Ala Met Asn Thr Pro Leu Gln
             740              745              750

Gly Ser Ala Ala Asp Ile Ile Lys Leu Ala Met Ile Asn Val Glu Lys
         755              760              765

Glu Leu Lys Ala Arg Lys Leu Lys Ser Arg Leu Leu Leu Ser Val His
     770              775              780

Asp Glu Leu Val Leu Glu Val Pro Ala Glu Glu Leu Glu Glu Val Lys
785              790              795              800

Ala Leu Val Lys Gly Val Met Glu Ser Val Val Glu Leu Lys Val Pro
             805              810              815

Leu Ile Ala Glu Val Gly Ala Gly Lys Asn Trp Tyr Glu Ala Lys
         820              825              830

<210> SEQ ID NO 7
<211> LENGTH: 831
<212> TYPE: PRT
<213> ORGANISM: Carboxydothermus islandicus

<400> SEQUENCE: 7

Met Gly Lys Val Val Leu Val Asp Gly Asn Ser Leu Leu His Arg Ala
1               5               10              15

Phe Phe Ala Leu Pro Pro Leu Lys Thr Thr Lys Gly Glu Pro Thr Gly
             20              25              30

Ala Val Tyr Gly Phe Leu Thr Met Leu Phe Arg Val Ile Arg Asp Glu
         35              40              45

Lys Pro Glu Tyr Leu Ala Val Ala Phe Asp Val Ser Arg Lys Thr Phe
     50              55              60

Arg Thr Glu Gln Phe Thr Ala Tyr Lys Gly His Arg Lys Glu Ala Pro
65              70              75              80

Asp Glu Leu Val Pro Gln Phe Ala Leu Val Arg Glu Val Leu Lys Val
             85              90              95

Leu Asn Val Pro Tyr Ile Glu Leu Asp Gly Tyr Glu Ala Asp Asp Ile
             100             105             110

Ile Gly His Leu Ser Arg Val Phe Ala Gly Gln Gly His Glu Val Val
         115             120             125

Ile Tyr Thr Ala Asp Arg Asp Met Leu Gln Leu Val Asp Glu Lys Thr
     130             135             140

Val Val Tyr Leu Thr Lys Lys Gly Ile Thr Glu Leu Val Lys Met Asp
145             150             155             160

Leu Ala Glu Val Leu Glu Asn Tyr Gly Leu Lys Pro Gln Gln Leu Val
             165             170             175

Asp Val Lys Gly Leu Met Gly Asp Pro Ser Asp Asn Ile Pro Gly Val
             180             185             190

Pro Gly Ile Gly Glu Lys Thr Ala Leu Asp Leu Ile Lys Thr Tyr Gly
         195             200             205

Ser Val Glu Glu Val Leu Ala Arg Lys Glu Glu Leu Lys Pro Lys Leu
     210             215             220

Arg Glu Lys Leu Ala Glu His Glu Ser Leu Ala Lys Ile Ser Lys Gln
225             230             235             240
```

-continued

Leu Ala Thr Ile Leu Arg Glu Ile Pro Leu Glu Ile Ser Leu Glu Asp
            245                 250                 255

Leu Lys Val Lys Glu Pro Asn Tyr Glu Glu Val Ala Lys Leu Phe Leu
        260                 265                 270

Arg Leu Glu Phe Lys Ser Phe Leu Lys Glu Ile Glu Pro Lys Ile Lys
        275                 280                 285

Asn Glu Tyr Gln Glu Ser Lys Glu Leu Val Gln Phe Glu Pro Val Ala
    290                 295                 300

Thr Glu Glu Arg Ile Ala Val Ile Phe Asn Asn Gly Phe Tyr Val Asp
305                 310                 315                 320

Asp Gly Glu Lys Thr Lys Phe Tyr Ser Leu Glu Gln Leu Phe Glu Ile
                325                 330                 335

Gln Glu Ile Phe Arg Asn Lys Lys Ile Ile Thr Asp Asp Ala Lys Gly
        340                 345                 350

Ile Tyr His Val Cys Leu Glu Lys Gly Leu Thr Phe Pro Glu Ile Cys
        355                 360                 365

Phe Asp Ala Arg Ile Ala Ala Tyr Val Leu Asn Pro Ala Asp Gln Asn
    370                 375                 380

Pro Gly Leu Lys Gly Leu Tyr Leu Lys Tyr Gly Leu Pro Val Phe Glu
385                 390                 395                 400

Asp Phe Ser Leu Asn Ile Arg Gly Leu Phe Tyr Leu Trp Lys Glu Met
            405                 410                 415

Met Glu Lys Val His Glu Gln Glu Gln Glu Arg Leu Phe Tyr Glu Ile
        420                 425                 430

Glu Leu Pro Leu Thr Pro Val Leu Ala Gln Met Glu His Thr Gly Ile
        435                 440                 445

Gln Val Asp Arg Glu Ala Leu Lys Glu Met Ser Val Glu Leu Gly Glu
    450                 455                 460

Gln Ile Glu Glu Leu Ile Arg Glu Ile Tyr Ala Leu Ala Gly Glu Glu
465                 470                 475                 480

Phe Asn Leu Asn Ser Pro Arg Gln Leu Gly Val Ile Leu Phe Glu Lys
            485                 490                 495

Leu Gly Leu Pro Val Ile Lys Lys Thr Lys Thr Gly Tyr Ser Thr Asp
        500                 505                 510

Ala Glu Val Leu Glu Glu Leu Leu Pro Tyr His Glu Ile Ile Gly Lys
        515                 520                 525

Ile Leu Thr Tyr Arg Gln Leu Met Lys Leu Lys Ser Thr Tyr Thr Asp
    530                 535                 540

Gly Leu Met Pro Leu Ile Asn Glu Arg Thr Gly Lys Leu His Thr Thr
545                 550                 555                 560

Phe Asn Gln Thr Gly Thr Leu Thr Gly Arg Leu Ala Ser Ser Glu Pro
            565                 570                 575

Asn Leu Gln Asn Ile Pro Val Arg Leu Glu Leu Gly Arg Lys Leu Arg
        580                 585                 590

Lys Met Phe Ile Pro Ser Pro Gly Tyr Asp Tyr Ile Val Ser Ala Asp
        595                 600                 605

Tyr Ser Gln Ile Glu Leu Arg Leu Leu Ala His Phe Ser Glu Glu Pro
    610                 615                 620

Lys Leu Ile Glu Ala Tyr Gln Lys Gly Glu Asp Ile His Arg Lys Thr
625                 630                 635                 640

Ala Ser Glu Val Phe Gly Val Pro Leu Glu Glu Val Thr Pro Glu Met
            645                 650                 655

Arg Ala His Ala Lys Ser Val Asn Tyr Gly Ile Val Tyr Gly Ile Ser

-continued

```
                    660                 665                 670

Asp Phe Gly Leu Gly Arg Asp Leu Lys Ile Pro Arg Glu Ile Ala Gly
            675                 680                 685

Lys Tyr Ile Lys Asn Tyr Phe Thr Asn Tyr Pro Arg Val Arg Glu Tyr
        690                 695                 700

Leu Asp Glu Leu Val Arg Thr Ala Arg Glu Lys Gly Tyr Val Thr Thr
705                 710                 715                 720

Leu Phe Gly Arg Arg Tyr Ile Pro Glu Leu Ser Ser Lys Asn Arg
                725                 730                 735

Thr Val Gln Gly Phe Gly Glu Arg Thr Ala Met Asn Thr Pro Leu Gln
            740                 745                 750

Gly Ser Ala Ala Asp Ile Ile Lys Leu Ala Met Ile Asn Val Glu Arg
        755                 760                 765

Glu Leu Lys Asn Ser Lys Leu Arg Ser Arg Leu Leu Leu Ser Val His
        770                 775                 780

Asp Glu Leu Val Leu Glu Val Pro Ala Glu Glu Leu Glu Glu Val Lys
785                 790                 795                 800

Gly Leu Val Lys Gly Val Met Glu Ser Val Val Glu Leu Lys Val Pro
                805                 810                 815

Leu Ile Ala Glu Val Gly Ala Gly Lys Asn Trp Tyr Glu Ala Lys
            820                 825                 830

<210> SEQ ID NO 8
<211> LENGTH: 586
<212> TYPE: PRT
<213> ORGANISM: Carboxydothermus pertinax

<400> SEQUENCE: 8

Met Gly Ile Pro Leu Glu Ile Ser Leu Glu Asp Leu Lys Val Lys Glu
1               5                   10                  15

Pro Asp Tyr Glu Glu Ala Ala Lys Leu Phe Thr Arg Leu Glu Phe Lys
            20                  25                  30

Ser Phe Leu Lys Glu Val Glu Pro Lys Val Lys Lys Glu Tyr Gln Glu
        35                  40                  45

Ser Lys Glu Thr Val Asn Ile Glu Ile Ile Lys Ala Glu Gly Gln Val
        50                  55                  60

Val Val Val Phe Asn Asp Gly Phe Tyr Val Asp Asp Gly Glu Lys Thr
65                  70                  75                  80

Ser Phe Tyr Ser Leu Asp Gln Leu Val Asp Leu Gln Glu Ile Phe Arg
                85                  90                  95

Gly Lys Glu Ile Ile Thr Asp Asp Ala Lys Gly Ile Tyr Arg Phe Cys
            100                 105                 110

Leu Glu Lys Gly Ile Ser Phe Pro Lys Val Asn Phe Asp Ala Arg Ile
        115                 120                 125

Ala Ala Tyr Val Leu Asn Pro Ala Asp Gln Asn Pro Gly Leu Asn Gly
        130                 135                 140

Leu Tyr Ile Lys Tyr Asn Leu Pro Val Tyr Asp Asp Leu Phe Leu Asn
145                 150                 155                 160

Ile Arg Gly Leu Phe Tyr Leu Lys Lys Glu Met Leu Ala Lys Ile Arg
                165                 170                 175

Glu Gln Gln Gln Glu Lys Leu Tyr Gln Glu Ile Glu Leu Pro Leu Thr
            180                 185                 190

Pro Val Leu Ala Arg Met Glu Phe Thr Gly Ile Gln Val Asp Arg Glu
        195                 200                 205
```

Ala Leu Lys Glu Met Ser Leu Glu Leu Gly Glu Gln Met Glu Ala Leu
    210             215                 220

Thr Arg Glu Ile Tyr Ser Leu Ala Gly Glu Glu Phe Asn Leu Asn Ser
225             230                 235                 240

Pro Lys Gln Leu Gly Val Ile Leu Phe Glu Lys Leu Gly Leu Pro Val
            245                 250                 255

Ile Lys Lys Thr Lys Thr Gly Tyr Ser Thr Asp Ala Glu Val Leu Glu
            260                 265                 270

Glu Leu Phe Ala Tyr His Glu Ile Val Gly Lys Ile Leu Asn Tyr Arg
            275                 280                 285

Gln Leu Met Lys Leu Lys Ser Thr Tyr Thr Asp Gly Leu Met Pro Leu
    290                 295                 300

Ile Asn Glu Tyr Thr Gly Lys Leu His Thr Thr Phe Asn Gln Thr Gly
305                 310                 315                 320

Thr Leu Thr Gly Arg Leu Ala Ser Ser Glu Pro Asn Leu Gln Asn Ile
                325                 330                 335

Pro Val Arg Leu Glu Leu Gly Arg Lys Leu Arg Lys Met Phe Ile Pro
            340                 345                 350

Ser Thr Gly Tyr Asp Tyr Ile Ile Ser Ala Asp Tyr Ser Gln Ile Glu
            355                 360                 365

Leu Arg Leu Leu Ala His Phe Ser Glu Glu Pro Lys Leu Ile Glu Ala
    370                 375                 380

Tyr Gln Lys Gly Glu Asp Ile His Arg Lys Thr Ala Ala Glu Val Phe
385                 390                 395                 400

Gly Val Pro Leu Glu Glu Val Ser Leu Glu Met Arg Ser His Ala Lys
            405                 410                 415

Ser Val Asn Tyr Gly Ile Val Tyr Gly Ile Ser Asp Phe Gly Leu Gly
            420                 425                 430

Arg Asp Leu Lys Ile Pro Arg Glu Val Ala Gly Lys Tyr Ile Lys Asn
    435                 440                 445

Tyr Phe Ala Asn Tyr Pro Lys Val Arg Glu Tyr Leu Asp Gly Leu Ile
    450                 455                 460

Arg Thr Ala Arg Glu Lys Gly Tyr Val Thr Thr Leu Phe Gly Arg Arg
465                 470                 475                 480

Arg Tyr Ile Pro Glu Leu Thr Ala Lys Asn Arg Thr Val Gln Ser Phe
            485                 490                 495

Gly Glu Arg Thr Ala Met Asn Thr Pro Leu Gln Gly Thr Ala Ala Asp
            500                 505                 510

Ile Ile Lys Leu Ala Met Ile Asn Met Glu Arg Glu Leu Leu Arg Lys
            515                 520                 525

Gly Leu Lys Ser Arg Leu Leu Leu Ser Val His Asp Glu Leu Val Leu
    530                 535                 540

Glu Val Pro Ala Glu Glu Val Glu Glu Val Lys Ser Leu Val Lys Lys
545                 550                 555                 560

Val Met Glu Ser Val Val Glu Leu Lys Val Pro Leu Ile Ala Glu Val
            565                 570                 575

Gly Met Gly Lys Asn Trp Tyr Glu Ala Lys
            580                 585

<210> SEQ ID NO 9
<211> LENGTH: 2496
<212> TYPE: DNA
<213> ORGANISM: Carboxydothermus pertinax

<400> SEQUENCE: 9

```
atgggaaaag tagttttggt tgatggaaat agtttattac atagagcctt ttttgccctg      60
ccgcccctaa aaacttccaa aggtgagcct accggggcgg tttacgggtt tttaaccatg     120
ctttttaaag tcataaaaga cgaaaatccc gattatctcg cggtggcctt tgatgttagc     180
cggaagactt tccgcagcga ccagtttttca gcttataaag gacaccgtaa ggaagctccc     240
gaggaactgg tacctcaatt tgccctggtg cgggaggtat taaaggtttt aaatattccc     300
tatatagagc ttatggggta cgaagctgat gatattatcg gccatttatc aaaggttttt     360
gtgaaccatg gccatgaggt aaaaatctat acggctgacc gggatatgtt acaattggta     420
gaggaaaaag tggcagttta ccttacgaag aaagggataa ccgatcttgt caaaatggat     480
ttagctaaag tgcaagaaaa ctatggctta aaaccgatcc agcttattga tgttaaaggc     540
ttaatgggag acccttcgga taatataccg ggagttcctg gaattggtga gaagaccgct     600
ttggatttaa tcaaaactta tggttcatta gaagaagttt tgacccataa agaggagttg     660
aaacccaaat taaagaaaa gcttaccgaa cacgaaaatt tagcaaaaat ttctaaagaa     720
ttagctacaa ttctgcggga gataccgtta gaaatttcct tggaggattt aaaagtcaaa     780
gaaccagatt atgaagaagc ggctaaactt tttacccgtt tagagtttaa aagcttctta     840
aaagaggtag aacccaaagt aaaaaaagaa taccaagaaa gcaaagagac ggtgaatatt     900
gaaattataa aggctgaagg ccaagtagtt gtggtcttta atgatggatt ttatgttgat     960
gatggagaaa agacaagttt ttactcttta gaccaattgg ttgatttgca agaaatcttc    1020
cggggaaaag aaatcataac cgatgatgcc aaaggaattt accgcttttg tctggaaaaa    1080
ggtatttctt ttcctaaagt gaattttgat gcaagaattg cagcgtatgt attaaatcct    1140
gccgaccaaa atccggggct taacggactg tatataaaat ataatttacc ggtgtatgac    1200 gaccttttt taaacattag aggtttattt tatctaaaaa aagaaatgct ggcgaaaata    1260
cgggaacagc agcaggaaaa gttatatcaa gaaattgaac ttccttaac tccggtccta    1320 gcccggatgg agtttaccgg cattcaggtg gatcgggaag ctttaaaaga gatgtcgtta    1380
gagcttgggg agcaaatgga agcgttaacc cgggaaatct attccctggc gggagaagag    1440
tttaatttaa actcgcccaa gcaattaggg gttatcctct ttgaaaaatt aggtctcccc    1500
gtaattaaga agacgaaaac cggctactct accgatgcgg aagtattaga agagcttttt    1560
gcgtatcatg aaattgtagg gaaaatatta aattaccggc agcttatgaa gttaaagtct    1620
acctataccg atggtttaat gcctttaatc aatgagtaca ccggtaaact tcatactact    1680
tttaatcaaa caggcacttt aaccggacgt ctggcctcct cggagcccaa tctccaaaat    1740
atccctgtgc ggctcgagct tgggcgtaaa ttgcgcaaaa tgtttattcc ttctacgggt    1800
tatgattata taatctcggc ggattattca caaattgagc taaggttact tgctcacttt    1860
tccgaagaac caaagttaat cgaagcgtac caaaaaggag aagatattca tcggaaaact    1920
gccgcggaag tgtttggggt acctttagag gaagtatctt tagaaatgcg gtctcatgct    1980
aaatcggtaa attttggtat tgtatacgga attagtgact ttgggcttgg cagggattta    2040
aaaattcccc gggaggttgc cgggaaatac attaaaaact attttgccaa ctatccaaag    2100
gttcgggagt atttagatgg gcttattcgg actgctagag aaaagggggta tgtgaccact    2160 ttatttggac gaaggcggta tattccggag ttaaccgcta aaaatcgtac agtacagagc    2220
tttggtgagc ggactgccat gaatacgccg ctccagggta ctgcggctga tataattaaa    2280
cttgcaatga ttaacatgga gagagagctt ttacggaagg ggttaaaatc ccggttgtta    2340
```

-continued ctttcggtgc acgacgaact tgttttagag gtaccggcag aggaagtgga ggaagtaaaa    2400
tccctggtaa aaaaggttat ggaatcagtg gtggaactaa aagttcccct gattgctgaa    2460
gttggcatgg ggaaaaactg gtatgaagct aaataa    2496

<210> SEQ ID NO 10
<211> LENGTH: 2496
<212> TYPE: DNA
<213> ORGANISM: Carboxydothermus ferrireducens

<400> SEQUENCE: 10
atgggaaaag tagtcctggt ggatggaaat agtttattac atagagcgtt ttttgccctt      60
ccgcccttaa aaactactaa aggagagcct accggggcgg tttacgggtt tttaacgatg     120
cttttcgggg taataaaaga tgaaaaaccc gaatatttag cggtagcctt tgatgttagc     180
cggaaaacct ttcgcaccaa gcagtttact gcatacaaag ggcaccgcaa agaagccccg     240
gatgagcttg taccccagtt tgccctggtg cgggaagtat taaaggtttt aaatgtgccc     300
tatattgaac ttgacggtta tgaggccgat gatattatcg ccacctatc aagggttttt     360 gcggggcaag acatgaagt ggtgatttat accgctgacc gggacatgct gcaactggta     420
gatgaaaaaa cggtggtata ccttaccaaa aaaggcatta ccgaactggt aaaaatggat     480
ttagctgcga tttttagaaag ctacggctta aaacccaaac agcttgtgga tgttaaagga     540
ttaatgggag atccctcgga caacataccc ggggttcccg ggattgggga gaaaactgct     600
ttagatttaa ttaaaactta tggctcagtg gaagaagttt tggcccataa agatgagtta     660
aaacctaaat taagagaaaa gcttgccgaa cacgaaaatt tagcaaaaat atcgaaacaa     720
ttagctacaa tcctgcggga ataccgtta gaaatctccc tggaagattt aaaagtgaaa     780
gaacctaatt atgaagaagt tgctaaatta tttcttcgcc ttgagtttaa aagctttta     840 aaagaaatag aaccaaaaat aaagaaagaa taccaggaag gtaaagattt ggtgcaattt     900
gaaactgtag aaacggaagg acagattgca gtagttttta gtgatggatt ttacgttgat     960
gacggggaaa aaacaaagtt ttactcgtta gaccggctga atgaaataca ggaaatattt    1020
aggaataaaa aaattattac cgacgatgcc aaaggaattt atcatgtctg tttagaaaaa    1080
ggtctgactt ttcccgaagt ttgttttgat gcgcggattg cagcttatgt tttaaacccg    1140
gccgaccaaa atcccggcct caagggctt tatctaaagt atgacttacc ggtgtatgaa    1200
gatgtatctt taaacattag agggttgttt tatttaaaaa aagaaatgat gaaaaaaatc    1260
tttgagcagg agcaggaaag gttattttat gaaatagaac ttccttaac tccagttctt    1320 gctcaaatgg agcataccgg cattcaggtt gaccgggaag cttttaaaga gatgtcgttg    1380
gagctgggag agcaaattga agagttaatc cgggaaattt atgcgctggc gggggaagag    1440
tttaacttaa attcgcccaa gcagctggga gttattcttt ttgaaaaact tgggctgccg    1500
gtaattaaaa agaccaagac gggctactct accgatgcgg aggttttgga gagagctcttg    1560 ccttaccacg aaattatcgg caaaatattg aattaccggc agcttatgaa gttaaaatcc    1620
acttatactg acggcttaat gccattaata aatgagcgta ccggtaaact tcacactact    1680
tttaaccaga ccggtacttt aaccggacgc ctggcgtctt cggagcccaa tctccaaaat    1740
attcccatcc ggttggaact cggtcggaaa ttacgcaaga tgtttatacc ttcaccgggg    1800
tatgattata ttgtttcggc ggattattcc cagattgaat taaggcttct tgcccatttt    1860
tccgaagagc ccaagcttat tgaagcttac caaaaagggg aggatattca ccggaaaaca    1920
gcctccgagg tgttcggtgt atctttggaa gaagttactc ccgagatgcg cgctcatgcc    1980

-continued

```
aagtcggtga acttcggcat tgtttatggc attagtgatt ttggtttagg cagagactta    2040
aagattcccc gggaggttgc cggtaagtac attaaaaatt attttgccaa ctatcccaaa    2100
gtgcgggagt atctcgatga acttgtccgt acggcaagag aaaagggtta tgtgaccact    2160
ttatttgggc gaagacgcta tattcctgag ctatcttcaa aaaaccgcac ggttcagggg    2220
tttggcgaaa ggacggccat gaatactccc cttcagggct cggctgccga tattattaag    2280
cttgcaatga ttaatgtaga aaaagaactt aaagcccgta agcttaagtc ccggctcctt    2340
ctttcggtgc acgatgagtt agttttagaa gtgccggcgg aagagctgga agaggtaaaa    2400
gcgctggtaa aagggggttat ggagtcggtg gttgaactga aagtgccttt aatcgctgaa    2460
gttggtgcag gcaaaaactg gtatgaagcg aagtaa                              2496
```

<210> SEQ ID NO 11
<211> LENGTH: 2496
<212> TYPE: DNA
<213> ORGANISM: Carboxydothermus islandicus

<400> SEQUENCE: 11

```
atgggaaaag tagtcctggt ggatggaaat agtttattac atagagcgtt ttttgccctt      60
ccgcctttaa aaactactaa aggggagcct accggggcgg tttacgggtt tttaacgatg     120
ctttttcggg taataagaga tgaaaaacca gaatatttag cggtagcttt tgatgttagc     180
cggaaaacct ttcgtaccga gcagtttact gcatacaaag ggcaccgcaa agaagctccg     240
gatgaactgg tacccagtt tgccctggta cgggaagtat taaaagtttt aaatgtgccc     300
tatattgaac ttgacggcta tgaggcagat gatattatcg gccacctatc aagggtgttt     360
gccgggcagg ggcatgaggt agtaatttac accgctgacc gggacatgct gcaactggtc     420
gatgaaaaaa ccgtggtata ccttaccaaa aaaggcatta ccgaactggt taaaatggat     480
ttagctgagg ttttggaaaa ctacggctta aaacctcagc agcttgtgga tgttaaagga     540
ttaatgggtg atccctcgga caacataccc ggagttccgg ggattgggga gaaaactgct     600
ttagatttaa taaaaactta tggctcggtg gaagaagttt tggcccgcaa agaagagtta     660
aaacctaaat taagagaaaa acttgccgaa catgaaagtt tagcgaaaat atcgaaacaa     720
ttagctacta tcctgcggga aataccgtta gaaatctccc tggaagattt aaaagtaaaa     780
gaacctaatt atgaagaagt agctaaatta tttcttcgcc ttgagtttaa aagctttta      840 aaagaaatag aaccaaaaat aaagaatgaa taccaggaaa gtaaagagtt ggtgcaattt     900
gaaccggtag caacgaaga acggattgcg gtaatcttta ataatggatt ttatgttgat     960 gacgggggaaa aaacaaagtt ttattcttta gaacagcttt ttgaaataca ggaaatattt    1020
cggaataaaa aaattattac cgacgacgcc aaaggaattt atcatgtctg tttagaaaaa    1080
ggtctgactt ttcccgaaat ttgttttgat gcgcggatag cagcttatgt tttaaatccg    1140
gccgaccaaa atcccgggct caagggggctg tatttaaagt atggtttgcc ggtgtttgaa    1200
gatttttctt taaatatcag gggtttattt tatttatgga agaaatgat ggaaaaagtt     1260 cacgagcagg agcaggaaag gttattttat gaaatagaac ttcctctaac tccggttctt    1320
gctcaaatgg agcataccgg cattcaggtt gaccggggaag ctttaaaaga aatgtcggtg    1380
gagctgggag agcaaattga agagttaatc cgggaaattt atgcgctggc gggggaagag    1440
tttaacttaa actctcccag gcagctggga gttattcttt ttgaaaaact tgggctgccg    1500
gtaattaaaa agaccaagac gggctactct accgatgcgg aggttttgga agagctttta    1560
```

-continued

| | | | | |
|---|---|---|---|---|
| ccttaccacg | aaattattgg | caaaattttg | acttaccgtc | agcttatgaa | gttaaaatca | 1620 |
| acctataccg | acggtttaat | gcctttaata | aatgagcgta | ccggtaaact | tcacaccact | 1680 |
| tttaaccaga | ccggtacctt | aaccggacgt | ctggcgtctt | cggagcccaa | tcttcaaaat | 1740 |
| attccggtgc | ggttggaact | cggccggaaa | ttacgcaaga | tgtttatacc | ttcccctggt | 1800 |
| tatgattata | ttgtttcggc | ggattattcc | cagattgagt | taaggcttct | tgctcatttt | 1860 |
| tccgaagagc | ccaagcttat | tgaagcgtac | caaaaagggg | aggatattca | ccggaaaacc | 1920 |
| gcttcagaag | tatttggtgt | acctttagaa | gaagttaccc | ctgagatgcg | tgctcatgcc | 1980 |
| aagtcggtga | acttcggcat | tgtctatggc | attagcgatt | ttggtttagg | cagagattta | 2040 |
| aagattcccc | gggagattgc | cggaaaatat | attaaaaatt | attttaccaa | ttatcccaga | 2100 |
| gtgcgggagt | atctcgatga | acttgtccgt | acggcaagag | aaaagggata | tgtgaccacg | 2160 |
| ttatttgggc | gaagacgtta | tattccggag | ctatcgtcca | aaaatcgcac | agtgcagggt | 2220 |
| tttggcgaaa | ggacggccat | gaataccccc | cttcagggct | cagctgccga | tattattaag | 2280 |
| cttgcaatga | ttaatgtaga | aagggaatta | aaaaacagca | agcttaggtc | ccggctcctt | 2340 |
| ctttcggtgc | acgatgagtt | agttttggaa | gtgccggcgg | aagagctgga | agaagttaaa | 2400 |
| gggctggtaa | aaggggttat | ggagtcggtg | gttgaactaa | aagtgccttt | aatcgctgaa | 2460 |
| gttggcgcag | gaaaaaactg | gtatgaagcc | aagtaa | | | 2496 |

<210> SEQ ID NO 12
<211> LENGTH: 1761
<212> TYPE: DNA
<213> ORGANISM: Carboxydothermus pertinax

<400> SEQUENCE: 12

| | | | | |
|---|---|---|---|---|
| atgggcatac | cgttagaaat | ttccttggag | gatttaaaag | tcaaagaacc | agattatgaa | 60 |
| gaagcggcta | aacttttac | ccgtttagag | tttaaaagct | tcttaaaaga | ggtagaaccc | 120 |
| aaagtaaaaa | aagaatacca | agaaagcaaa | gagacggtga | atattgaaat | tataaaggct | 180 |
| gaaggccaag | tagttgtggt | ctttaatgat | ggattttatg | ttgatgatgg | agaaaagaca | 240 |
| agttttact | ctttagacca | attggttgat | ttgcaagaaa | tcttccgggg | aaaagaaatc | 300 |
| ataaccgatg | atgccaaagg | aatttaccgc | ttttgtctgg | aaaaaggtat | ttcttttcct | 360 |
| aaagtgaatt | ttgatgcaag | aattgcagcg | tatgtattaa | atcctgccga | ccaaaatccg | 420 |
| gggcttaacg | gactgtatat | aaaatataat | ttaccggtgt | atgacgacct | ttttttaaac | 480 |
| attagaggtt | tattttatct | aaaaaaagaa | atgctggcga | aaatacggga | acagcagcag | 540 |
| gaaaagttat | atcaagaaat | tgaacttcct | ttaactccgg | tcctagcccg | gatggagttt | 600 |
| accggcattc | aggtggatcg | ggaagcttta | aagagatgt | cgttagagct | tggggagcaa | 660 |
| atggaagcgt | taacccggga | aatctattcc | ctggcgggag | aagagtttaa | tttaaactcg | 720 |
| cccaagcaat | taggggttat | cctctttgaa | aaattaggtc | tccccgtaat | taagaagacg | 780 |
| aaaaccggct | actctaccga | tgcggaagta | ttagaagagc | tttttgcgta | tcatgaaatt | 840 |
| gtagggaaaa | tattaaatta | ccggcagctt | atgaagttaa | agtctaccta | taccgatggt | 900 |
| ttaatgcctt | taatcaatga | gtacaccggt | aaacttcata | ctactttaa | tcaaacaggc | 960 |
| actttaaccg | gacgtctggc | ctcctcggag | cccaatctcc | aaaatatccc | tgtgcggctc | 1020 |
| gagcttgggc | gtaaattgcg | caaaatgttt | attccttcta | cgggttatga | ttatataatc | 1080 |
| tcggcggatt | attcacaaat | tgagctaagg | ttacttgctc | actttccgaa | agaaccaaag | 1140 |
| ttaatcgaag | cgtaccaaaa | aggagaagat | attcatcgga | aaactgccgc | ggaagtgttt | 1200 |

-continued

```
ggggtacctt tagaggaagt atctttagaa atgcggtctc atgctaaatc ggtaaatttt    1260
ggtattgtat acggaattag tgactttggg cttggcaggg atttaaaaat tccccgggag    1320
gttgccggga aatacattaa aaactatttt gccaactatc caaaggttcg ggagtattta    1380
gatgggctta ttcggactgc tagagaaaag gggtatgtga ccactttatt tggacgaagg    1440
cggtatattc cggagttaac cgctaaaaat cgtacagtac agagctttgg tgagcggact    1500
gccatgaata cgccgctcca gggtactgcg gctgatataa ttaaacttgc aatgattaac    1560
atggagagag agcttttacg gaaggggtta aaatcccggt tgttactttc ggtgcacgac    1620
gaacttgttt tagaggtacc ggcagaggaa gtggaggaag taaaatccct ggtaaaaaag    1680
gttatggaat cagtggtgga actaaaagtt cccctgattg ctgaagttgg catggggaaa    1740
aactggtatg aagctaaata a                                              1761
```

<210> SEQ ID NO 13
<211> LENGTH: 2496
<212> TYPE: DNA
<213> ORGANISM: Carboxydothermus pertinax

<400> SEQUENCE: 13

```
atgggaaaag tagttttggt tgatggaaat agtttattac atagagcctt ttttgccctg     60
ccgcccctaa aaacttccaa aggtgagcct accggggcgg tttacgggtt tttaaccatg    120 cttttttaaag tcataaaaga cgaaaatccc gattatctcg cggtggcctt tgatgttagc    180
cggaagactt ccgcagcga ccagtttttca gcttataaag acaccgtaa ggaagctccc    240 gaggaactgg tacctcaatt tgccctggtg cgggaggtat taaaggtttt aaatattccc    300
tatatagagc ttatggggta cgaagctgat gatattatcg gccatttatc aaaggttttt    360
gtgaaccatg ccatgaggt aaaaatctat acggctgacc gggatatgtt acaattggta    420
gaggaaaaag tggcagttta ccttacgaag aaagggataa ccgatcttgt caaaatggat    480
ttagctaaag tgcaagaaaa ctatggctta aaaccgatcc agcttattga tgttaaaggc    540
ttaatgggag acccttcgga taatataccg ggagttcctg gaattggtga gaagaccgct    600
ttggatttaa tcaaaactta tggttcatta gaagaagttt tgacccataa agaggagttg    660
aaacccaaat taaagaaaa gcttaccgaa cacgaaaatt tagcaaaaat ttctaaagaa    720
ttagctacaa ttctgcggga gataccgtta gaaatttcct tggaggattt aaaagtcaaa    780
gaaccagatt atgaagaagc ggctaaactt tttacccgtt tagagtttaa aagcttctta    840
aaagaggtag aacccaaagt aaaaaaagaa taccaagaaa gcaaagagac ggtgaatatt    900
gaaattataa aggctgaagg ccaagtagtt gtggtcttta atgatggatt ttatgttgat    960
gatggagaaa agacaagttt ttactctta gaccaattgg ttgatttgca agaaatcttc   1020
cggggaaaag aaatcataac cgatgatgcc aaaggaattt accgcttttg tctggaaaaa   1080 ggtattctt ttcctaaagt gaattttgat gcaagaattg cagcgtatgt attaaatcct   1140
gccgaccaaa atccggggct taacggactg tatataaaat ataatttacc ggtgtatgac   1200 gaccttttt taaacattag aggtttattt tatctaaaaa aagaaatgct ggcgaaaata   1260
cgggaacagc agcaggaaaa gttatatcaa gaaattgaac ttcctttaac tccggtccta   1320
gcccggatgg agtttaccgg cattcaggtg gatcgggaag ctttaaaaga gatgtcgtta   1380
gagcttgggg agcaaatgga agcgttaacc cgggaaatct attccctggc gggagaagag   1440
tttaatttaa actcgcccaa gcaattaggg gttatcctct ttgaaaaatt aggtctcccc   1500
```

-continued

```
gtaattaaga agacgaaaac cggctactct accgatgcgg aagtattaga agagcttttt    1560
gcgtatcatg aaattgtagg gaaaatatta aattaccggc agcttatgaa gttaaagtct    1620
acctataccg atggtttaat gcctttaatc aatgagtaca ccggtaaact tcatactact    1680
tttaatcaaa caggcacttt aaccggacgt ctggcctcct cggagcccaa tctccaaaat    1740
atccctgtgc ggctcgagct tgggcgtaaa ttgcgcaaaa tgtttattcc ttctacgggt    1800
tatgattata taatctcggc ggattattca caaattgagc taaggttact tgctcacttt    1860
tccgaagaac caaagttaat cgaagcgtac caaaaaggag aagatattca tcggaaaact    1920
gccgcggaag tgtttggggt acctttagag gaagtatctt tagaaatgcg gtctcatgct    1980
aaatcggtaa attatggtat tgtatacgga attagtgact ttgggcttgg cagggattta    2040
aaaattcccc gggaggttgc cgggaaatac attaaaaact attttgccaa ctatccaaag    2100
gttcgggagt atttagatgg gcttattcgg actgctagag aaaaggggta tgtgaccact    2160
ttatttggac gaaggcggta tattccggag ttaaccgcta aaaatcgtac agtacagagc    2220
tttggtgagc ggactgccat gaatacgccg ctccagggta ctgcggctga tataattaaa    2280
cttgcaatga ttaacatgga gagagagctt ttacggaagg ggttaaaatc ccggttgtta    2340
ctttcggtgc acgacgaact tgtttttagag gtaccggcag aggaagtgga ggaagtaaaa    2400
tccctggtaa aaaaggttat ggaatcagtg gtggaactaa aagttcccct gattgctgaa    2460
gttggcatgg ggaaaaactg gtatgaagct aaataa                              2496
```

```
<210> SEQ ID NO 14
<211> LENGTH: 2496
<212> TYPE: DNA
<213> ORGANISM: Carboxydothermus ferrireducens

<400> SEQUENCE: 14
atgggaaaag tagtcctggt ggatggaaat agtttattac atagagcgtt ttttgccctt      60
ccgcccttaa aaactactaa aggagagcct accggggcgg tttacgggtt tttaacgatg     120 cttttttcggg taataaaaga tgaaaaaccc gaatatttag cggtagcctt tgatgttagc     180
cggaaaacct ttcgcaccaa gcagtttact gcatacaaag ggcaccgcaa agaagccccg     240
gatgagcttg taccccagtt tgccctggtg cgggaagtat taaaggtttt aaatgtgccc     300
tatattgaac ttgacggtta tgaggccgat gatattatcg gccacctatc aagggttttt     360
gcggggcaag gacatgaagt ggtgatttat accgctgacc gggacatgct gcaactggta     420
gatgaaaaaa cggtggtata ccttaccaaa aaaggcatta ccgaactggt taaaatggat     480
ttagctgcga tttttagaaag ctacggctta aaacccaaac agcttgtgga tgttaaagga     540
ttaatgggag atccctcgga caacataccc ggggttcccg ggattgggga gaaaactgct     600
ttagatttaa ttaaaactta tggctcagtg aagaagtttt ggcccataa agatgagtta      660 aaacctaaat taagagaaaa gcttgccgaa cacgaaaatt tagcaaaaat atcgaaacaa     720
ttagctacaa tcctgcggga aataccgtta gaaatctccc tggaagattt aaaagtgaaa     780
gaacctaatt atgaagaagt tgctaaatta tttcttcgcc ttgagtttaa aagcttttta     840
aaagaaatag aaccaaaaat aaagaaagaa taccaggaag gtaaagattt ggtgcaattt     900
gaaactgtag aaacggaagg acagattgca gtagttttta gtgatggatt ttacgttgat     960
gacggggaaa aaacaaagtt ttactcgtta gaccggctga atgaaataca ggaaatattt    1020
aggaataaaa aaattattac cgacgatgcc aaaggaattt atcatgtctg tttagaaaaa    1080
ggtctgactt ttcccgaagt ttgttttgat gcgcggattg cagcttatgt tttaaacccg    1140
```

```
gccgaccaaa atcccggcct caaggggctt tatctaaagt atgacttacc ggtgtatgaa      1200
gatgtatctt taaacattag agggttgttt tatttaaaaa aagaaatgat gaaaaaaatc      1260
tttgagcagg agcaggaaag gttattttat gaaatagaac ttcctttaac tccagttctt      1320
gctcaaatgg agcataccgg cattcaggtt gaccggggag ctttaaaaga gatgtcgttg      1380
gagctgggag agcaaattga agagttaatc cgggaaattt atgcgctggc gggggaagag      1440
tttaacttaa attcgcccaa gcagctggga gttattcttt ttgaaaaact tgggctgccg      1500
gtaattaaaa agaccaagac gggctactct accgatgcgg aggtttttgga agagctcttg      1560 ccttaccacg aaattatcgg caaaatattg aattaccggc agcttatgaa gttaaaatcc      1620
acttatactg acggcttaat gccattaata aatgagcgta ccggtaaact tcacactact      1680
tttaaccaga ccggtacttt aaccggacgc ctggcgtctt cggagcccaa tctccaaaat      1740
attcccatcc ggttggaact cggtcggaaa ttacgcaaga tgtttatacc ttcaccgggg      1800
tatgattata ttgtttcggc ggattattcc cagattgaat taaggcttct tgcccatttt      1860
tccgaagagc ccaagcttat tgaagcttac caaaaagggg aggatattca ccggaaaaca      1920
gcctccgagg tgttcggtgt atctttggaa gaagttactc ccgagatgcg cgctcatgcc      1980
aagtcggtga actacggcat tgtttatggc attagtgatt ttggtttagg cagagactta      2040
aagattcccc gggaggttgc cggtaagtac attaaaaatt attttgccaa ctatcccaaa      2100
gtgcgggagt atctcgatga acttgtccgt acggcaagag aaaagggtta tgtgaccact      2160
ttatttgggc gaagacgcta tattcctgag ctatcttcaa aaaccgcac ggttcaggggg      2220 tttggcgaaa ggacggccat gaatactccc cttcagggct cggctgccga tattattaag      2280
cttgcaatga ttaatgtaga aaaagaactt aaagcccgta agcttaagtc ccggctcctt      2340
ctttcggtgc acgatgagtt agtttttagaa gtgccggcgg aagagctgga agaggtaaaa      2400
gcgctggtaa aaggggttat ggagtcggtg gttgaactga aagtgccttt aatcgctgaa      2460
gttggtgcag gcaaaaactg gtatgaagcg aagtaa                                2496
```

```
<210> SEQ ID NO 15
<211> LENGTH: 2496
<212> TYPE: DNA
<213> ORGANISM: Carboxydothermus islandicus

<400> SEQUENCE: 15
atgggaaaag tagtcctggt ggatggaaat agtttattac atagagcgtt ttttgccctt        60
ccgcctttaa aaactactaa aggggagcct accggggcgg tttacgggtt tttaacgatg       120
ctttttcggg taataagaga tgaaaaacca gaatatttag cggtagcttt tgatgttagc       180
cggaaaacct ttcgtaccga gcagtttact gcatacaaag gcaccgcaa agaagctccg       240 gatgaactgg taccccagtt tgccctggta cgggaagtat taaaagtttt aaatgtgccc       300
tatattgaac ttgacggcta tgaggcagat gatattatcg gccacctatc aagggtgttt       360
gccgggcagg ggcatgaggt agtaatttac accgctgacc gggacatgct gcaactggtc       420
gatgaaaaaa ccgtggtata ccttaccaaa aaaggcatta ccgaactggt taaaatggat       480
ttagctgagg ttttggaaaa ctacggctta aaacctcagc agcttgtgga tgttaaagga       540
ttaatgggtg atccctcgga caacataccc ggagttccgg ggattgggga gaaaactgct       600
ttagatttaa taaaaactta tggctcggtg gaagaagttt tggcccgcaa agaagagtta       660
aaacctaaat taagagaaaa acttgccgaa catgaaagtt tagcgaaaat atcgaaacaa       720
```

-continued

```
ttagctacta tcctgcggga aataccgtta gaaatctccc tggaagattt aaaagtaaaa        780
gaacctaatt atgaagaagt agctaaatta tttcttcgcc ttgagtttaa aagctttta        840 aaagaaatag aaccaaaaat aaagaatgaa taccaggaaa gtaaagagtt ggtgcaattt        900
gaaccggtag caacggaaga acggattgcg gtaatcttta ataatggatt ttatgttgat        960 gacgggaaa aaacaaagtt ttattcttta gaacagcttt ttgaaataca ggaaatattt       1020
cggaataaaa aaattattac cgacgacgcc aaaggaattt atcatgtctg tttagaaaaa       1080
ggtctgactt ttcccgaaat ttgttttgat gcgcggatag cagcttatgt tttaaatccg       1140
gccgaccaaa atcccgggct caaggggctg tatttaaagt atggtttgcc ggtgtttgaa       1200
gatttttctt taaatatcag gggtttattt tatttatgga agaaatgat ggaaaaagtt       1260 cacgagcagg agcaggaaag gttattttat gaaatagaac ttcctctaac tccggttctt       1320
gctcaaatgg agcataccgg cattcaggtt gaccgggaag ctttaaaaga aatgtcggtg       1380
gagctgggag agcaaattga agagttaatc cgggaaattt atgcgctggc gggggaagag       1440
tttaacttaa actctcccag gcagctggga gttattcttt ttgaaaaact tgggctgccg       1500
gtaattaaaa agaccaagac gggctactct accgatgcgg aggttttgga agagctttta       1560
ccttaccacg aaattattgg caaaattttg acttaccgtc agcttatgaa gttaaaatca       1620
acctataccg acggtttaat gcctttaata aatgagcgta ccggtaaact tcacaccact       1680
tttaaccaga ccggtacctt aaccggacgt ctggcgtctt cggagcccaa tcttcaaaat       1740
attccggtgc ggttggaact cggccggaaa ttacgcaaga tgtttatacc ttcccctggt       1800
tatgattata ttgtttcggc ggattattcc cagattgagt taaggcttct tgctcatttt       1860
tccgaagagc ccaagcttat tgaagcgtac caaaaagggg aggatattca ccggaaaacc       1920
gcttcagaag tatttggtgt acctttagaa gaagttaccc ctgagatgcg tgctcatgcc       1980
aagtcggtga actacggcat tgtctatggc attagcgatt ttggtttagg cagagattta       2040
aagattcccc gggagattgc cggaaaatat attaaaaatt attttaccaa ttatcccaga       2100
gtgcgggagt atctcgatga acttgtccgt acggcaagag aaaagggata tgtgaccacg       2160
ttatttgggc gaagacgtta tattccggag ctatcgtcca aaaatcgcac agtgcagggt       2220
tttggcgaaa ggacggccat gaataccccc cttcagggct cagctgccga tattattaag       2280
cttgcaatga ttaatgtaga aagggaatta aaaaacagca agcttaggtc ccggctcctt       2340
ctttcggtgc acgatgagtt agttttggaa gtgccggcgg aagagctgga agaagttaaa       2400
gggctggtaa aaggggttat ggagtcggtg gttgaactaa aagtgccttt aatcgctgaa       2460
gttggcgcag gaaaaaactg gtatgaagcc aagtaa                                 2496
```

```
<210> SEQ ID NO 16
<211> LENGTH: 1761
<212> TYPE: DNA
<213> ORGANISM: Carboxydothermus pertinax

<400> SEQUENCE: 16
atgggcatac cgttagaaat ttccttggag gatttaaaag tcaaagaacc agattatgaa         60
gaagcggcta aacttttac ccgtttagag tttaaaagct tcttaaaaga ggtagaaccc        120
aaagtaaaaa aagaatacca agaaagcaaa gagacggtga atattgaaat tataaaggct        180
gaaggccaag tagttgtggt ctttaatgat ggatttatg ttgatgatgg agaaaagaca        240 agttttact ctttagacca attggttgat ttgcaagaaa tcttccgggg aaaagaaatc        300
ataaccgatg atgccaaagg aatttaccgc ttttgtctgg aaaaaggtat ttctttttcct        360
```

-continued

```
aaagtgaatt ttgatgcaag aattgcagcg tatgtattaa atcctgccga ccaaaatccg      420
gggcttaacg gactgtatat aaaatataat ttaccggtgt atgacgacct tttttaaac      480 attagaggtt tattttatct aaaaaaagaa atgctggcga aaatacggga acagcagcag      540
gaaaagttat atcaagaaat tgaacttcct ttaactccgg tcctagcccg gatggagttt      600
accggcattc aggtggatcg ggaagcttta aaagagatgt cgttagagct tggggagcaa      660
atggaagcgt taacccggga aatctattcc ctggcgggag aagagtttaa tttaaactcg      720
cccaagcaat tagggggttat cctctttgaa aaattaggtc tccccgtaat taagaagacg      780
aaaaccggct actctaccga tgcggaagta ttagaagagc tttttgcgta tcatgaaatt      840
gtagggaaaa tattaaatta ccggcagctt atgaagttaa agtctaccta taccgatggt      900
ttaatgcctt taatcaatga gtacaccggt aaacttcata ctacttttaa tcaaacaggc      960
actttaaccg gacgtctggc ctcctcggag cccaatctcc aaaatatccc tgtgcggctc     1020
gagcttgggc gtaaattgcg caaaatgttt attccttcta cgggttatga ttatataatc     1080
tcggcggatt attcacaaat tgagctaagg ttacttgctc acttttccga agaaccaaag     1140
ttaatcgaag cgtaccaaaa aggagaagat attcatcgga aaactgccgc ggaagtgttt     1200
ggggtacctt tagaggaagt atctttagaa atgcggtctc atgctaaatc ggtaaattat     1260
ggtattgtat acggaattag tgactttggg cttggcaggg atttaaaaat tccccgggag     1320
gttgccggga aatacattaa aaactatttt gccaactatc caaaggttcg ggagtattta     1380
gatgggctta ttcggactgc tagagaaaag gggtatgtga ccactttatt tggacgaagg     1440
cggtatattc cggagttaac cgctaaaaat cgtacagtac agagctttgg tgagcggact     1500
gccatgaata cgccgctcca gggtactgcg gctgatataa ttaaacttgc aatgattaac     1560
atggagagag agctttttacg gaaggggtta aaatcccggt tgttactttc ggtgcacgac     1620
gaacttgttt tagaggtacc ggcagaggaa gtggaggaag taaaatccct ggtaaaaaag     1680
gttatggaat cagtggtgga actaaaagtt cccctgattg ctgaagttgg catggggaaa     1740
aactggtatg aagctaaata a                                              1761
```

```
<210> SEQ ID NO 17
<211> LENGTH: 25
<212> TYPE: DNA
<213> ORGANISM: Homo sapiens

<400> SEQUENCE: 17
caaccgcgag aagatgaccc agatc                                            25

<210> SEQ ID NO 18
<211> LENGTH: 25
<212> TYPE: DNA
<213> ORGANISM: Homo sapiens

<400> SEQUENCE: 18
gcaacgtaca tggctggggt gttga                                            25

<210> SEQ ID NO 19
<211> LENGTH: 25
<212> TYPE: DNA
<213> ORGANISM: Homo sapiens

<400> SEQUENCE: 19
caaccgcgag aagatgaccc agatc                                            25
```

US 12,692,525 B1

73

74

-continued

<210> SEQ ID NO 20
<211> LENGTH: 25
<212> TYPE: DNA
<213> ORGANISM: Homo sapiens

<400> SEQUENCE: 20
ttcccgctcg gccgtggtgg tgaag                                    25

<210> SEQ ID NO 21
<211> LENGTH: 25
<212> TYPE: DNA
<213> ORGANISM: Homo sapiens

<400> SEQUENCE: 21
caaccgcgag aagatgaccc agatc                                    25

<210> SEQ ID NO 22
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddCMP

<400> SEQUENCE: 22
gcaacgtaca tggctggggt gttgaaggtn                               30

<210> SEQ ID NO 23
<211> LENGTH: 25
<212> TYPE: DNA
<213> ORGANISM: Homo sapiens

<400> SEQUENCE: 23
caaccgcgag aagatgaccc agatc                                    25

<210> SEQ ID NO 24
<211> LENGTH: 30
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is ddCMP

<400> SEQUENCE: 24
acagtgtggg tgaccccgtc accggagtcn                               30

<210> SEQ ID NO 25
<211> LENGTH: 28
<212> TYPE: DNA
<213> ORGANISM: COVID-19 virus
<220> FEATURE:
<221> NAME/KEY: misc_feature
<222> LOCATION: (28)..(28)
<223> OTHER INFORMATION: n is ddCMP

<400> SEQUENCE: 25
gagggagcct tgaatacacc aaaagatn                                 28

<210> SEQ ID NO 26
<211> LENGTH: 28
<212> TYPE: DNA
<213> ORGANISM: COVID-19 virus
<220> FEATURE:
<221> NAME/KEY: misc_feature -continued

```
<222> LOCATION: (28)..(28)
<223> OTHER INFORMATION: n is ddCMP

<400> SEQUENCE: 26
gttgtagcac gattgcagca ttgttagn                                          28

<210> SEQ ID NO 27
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddCMP

<400> SEQUENCE: 27
agaagatgac ccagatcatg tttgagan                                          28

<210> SEQ ID NO 28
<211> LENGTH: 27
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is ddCMP

<400> SEQUENCE: 28
ttacagggat agcacagcct ggatagn                                           27
```

THERMOSTABLE PURIFIED REVERSE TRANSCRIPTASE AND METHODS OF USE

CROSS-REFERENCE TO RELATED APPLICATIONS

This non-provisional application claims priority from U.S. provisional patent application No. 63/124,055, filed on Dec. 11, 2020.

SEQUENCE LISTING

This application contains Sequence Listing entitled SequenceListing_Dec_2020.txt, which is submitted in ASCII text format and is hereby incorporated by reference in its entirety.

BACKGROUND

The present invention relates to the field of molecular biology and particularly to thermostable reverse transcription and applications to RT-PCR and RT-PAP amplifications using ribonucleic acid (RNA) templates.

Classification

"Heat-loving" or thermostable microorganisms thrive at high temperatures ≥50° C. Many such microorganisms are archaea, though they can be bacteria such as *Carboxydothermus* pertinax. One classification sorts these organisms into three distinct subtypes according to their optimal growth temperatures: 1) thermophiles with optimal temperatures between 50° C. and 64° C., 2) extreme thermophiles with optimal growth temperatures between 65° C. and 80° C., and 3) hyperthermophiles with optimal growth temperatures above 80° C.

Accordingly, their thermostable DNA polymerases (i.e., DNA-dependent DNA polymerases and RNA-dependent DNA polymerases or reverse transcriptases) can also be classified into three subtypes based on their optimal reaction temperatures: 1) thermophilic DNA polymerases with optimal reaction temperatures between 50° C. and 64° C., 2) extreme thermophilic DNA polymerases with optimal reaction temperatures between 65° C. and 80° C., and 3) hyperthermophilic DNA polymerases with optimal reaction temperatures above 80° C.

Herein, examples of thermophilic DNA-dependent DNA polymerases were found functioning as thermophilic RNA-dependent DNA polymerases or reverse transcriptases as well are disclosed.

DNA Polymerase

DNA polymerase refers to a polymerase characterized as catalyzing synthesis, polymerization or extension of deoxyribonucleic acids in 5' to 3' direction. DNA polymerase requires a primer to initiate the synthesis of a DNA strand along a complementary nucleic acid template:

$$[dNMP]_n + dNTP \rightarrow [dNMP]_{n+1} + PPi$$

DNA-Dependent DNA Polymerase

DNA-dependent DNA polymerase refers to a polymerase characterized as catalyzing DNA polymerization or extension using a DNA template.

Based on sequence homology with *E. coli* and other organisms, DNA-dependent DNA polymerases can be divided into six families: A, B, C, D, X and Y.

RNA-Dependent DNA Polymerase or Reverse Transcriptase

Retroviruse can encode a special DNA polymerase called reverse transcriptase. It is characterized as catalyzing DNA polymerization or extension using a RNA template.

AMV and MMLV reverse transcriptases, commonly used mesophilic retroviral transcriptases at optimal temperatures of 42° C. and 37° C., are isolated from Avian myeloblastosis virus (AMV) and moloney murine leukemia virus (MMLV) (Verma, 1977). However, at mesophilic temperatures, a RNA template keeps its secondary structures, resulting in premature termination of the reverse-transcribed DNA product.

Native Taq, a thermostable DNA-dependent DNA polymerase, is found to have measurable reverse transcriptase activity particularly in the presence of manganese ions (Jones and Foulkes, 1989). rTth, another thermostable DNA-dependent DNA polymerase, particularly in the presence of manganese ions, shows over 100-fold greater reverse transcriptase activity than Taq, even though they have no significant amino acid sequence similarity (Myers and Gelfand, 199, Smith, et al., 2007). However, these DNA polymerases show low reverse transcriptase activities, leading to low efficiency of reverse transcription. In addition, they use Manganese ion, leading to low fidelity of reverse transcription.

Pyrophorolysis

DNA polymerase can also catalyze pyrophosphorolysis, which is the reverse reaction of deoxyribonucleic acid (DNA) polymerization. In the presence of pyrophosphate, the 3' nucleotide is removed by DNA polymerase from duplex DNA to generate a triphosphate nucleotide and a 3' shortened duplex DNA (Deutscher and Kornberg, 1969):

$$[dNMP]_n + PPi \rightarrow [dNMP]_{n-1} + dNTP$$

DNA-Dependent DNA Pyrophosphorolysis

Taq, Tfl, TaqFS, Pfu and Vent DNA polymerases can catalyze DNA-dependent DNA pyrophosphorolysis using DNA templates (Liu and Sommer, 2000, Liu and Sommer, 2002, Liu and Sommer, 2004a, Gardner et al., 2004). HIV and HCV reverse transcriptases were also reported to catalyze DNA-dependent DNA pyrophosphorolysis that removes 3' dideoxynucleotide from DNA primer on a synthetic DNA (rather than RNA) template (Arion, et al., 1998 and Urban, et al., 2001).

RNA-Dependent DNA Pyrophosphorolysis

Besides DNA template, mutant Taq DNA polymerase having a F667Y mutation can catalyze RNA-dependent DNA pyrophosphorolysis that removes 3' dideoxyribonucleotide or 3' acyclonucleotide from a primer using a RNA template. However, the efficiency is still relatively low (U.S. Pat. Nos. 9,133,491, 9,926,543).

Application to Nucleic Acid Amplification

PCR and RT-PCR

PCR refers to polymerase chain reaction, a widely used method for nucleotide acid amplification. In PCR, DNA polymerase, such as Taq, amplifies a DNA template exponentially to billions of copies.

RT-PCR refers to reverse-transcription PCR. RT-PCR includes two steps of 1) reverse transcription on a RNA template to produce cDNA by typically a non-thermostable viral reverse transcriptase, such as MMLV or AMV-RT, and 2) PCR amplification of the cDNA as template by a thermostable DNA-dependent DNA polymerase, such as Taq.

The current RT-PCR has three drawbacks. 1) At mesophilic temperatures: non-thermostable viral reverse transcriptases could not pass through a RNA template of stable secondary structures, resulting in premature termination. 2) Inhibition of downstream PCR: AMV and MMLV reverse transcriptases used in RT step inhibit the downstream PCR amplification, decreasing its efficiency. 3) Two step/tube procedure: due to incompatibility of reaction compositions, reverse transcription is conducted in a first tube and then PCR in a second tube, increasing potential contamination.

PAP and RT-PAP (RNA-PAP)

Pyrophosphorolysis activated polymerization (PAP) is a method for nucleic acid amplification where pyrophosphorolysis and polymerization are serially coupled by DNA polymerase using 3' blocked primers (Liu and Sommer, 2000). A primer is blocked at the 3' end with a non-extendable nucleotide (3' blocker), such as a 3' dideoxy-nucleotide, and cannot be directly extended by DNA polymerase. When the 3' blocked primer anneals to its complementary DNA template, DNA polymerase can remove the 3' blocker from the 3' blocked primer in the presence of pyrophosphate, which reaction is pyrophospho-rolysis. The DNA polymerase can then extend the 3' unblocked primer on the DNA template. In addition to references cited herein, PAP has been described in U.S. Pat. Nos. 6,534,269, 7,033,763, 7,105,298, 7,238,480, 7,504, 221, 7,914,995 and 7,919,253.

Besides 3' dideoxynucleotides, other 3' blockers, such as acyclonucleotides that substitute a 2-hydroxyethoxymethyl group for the 2'-deoxyribofuranosyl sugar, are also used (Liu and Sommer, 2004a).

The serial coupling of pyrophosphorolysis and extension using the 3' blocked primer in PAP results in an extremely high selectivity (Liu and Sommer, 2000, Liu and Sommer, 2004b) because a significant nonspecific amplification (false positive) requires mismatch pyrophosphorolysis followed by mis-incorporation by the DNA polymerase, an event with a frequency estimated to be $3.3 \times 10^{-11}$.

DNA-PAP

PAP was initially tested with Tfl and Taq DNA-dependent DNA polymerases using a DNA template of the human dopamine D1 gene, proving the principle that DNA-dependent DNA pyrophosphorolysis and DNA-dependent DNA polymerization can be serially coupled (Liu and Sommer, 2000) for amplification. The efficiency of PAP was greatly improved using TaqFS, a genetically engineered polymerase comprising a F667Y mutation, which were demonstrated using many other DNA templates (Liu and Sommer, 2002).

RT-PAP (RNA-PAP)

RT-PAP was developed that can directly amplify a RNA template. RT-PAP brings in a new mechanism for amplification of the RNA template in which RNA-dependent DNA pyrophosphorolysis removes the 3' blocker, such as 3' dide-oxynucleotide, from a blocked primer when hybridized to the RNA template, and then RNA-dependent DNA polym-erization extends the unblocked primer (U.S. Pat. Nos. 9,133,491, 9,926,543). Due to the low efficiency, until now there has been no commercial use.

Advantages of the Invention

RT-PCR: Thermostable purified DNA-dependent DNA polymerases efficiently catalyze reverse transcription on a RNA template at thermophilic temperatures, virtually also being reverse transcriptases or RNA-dependent DNA poly-merases. Besides reverse transcription at thermophilic tem-peratures, it is advantageous that this RT-PCR integrates RT step and PCR step into a single tube, and use Magnesium ion rather than Manganese ion for high fidelity of amplification.

RT-PAP: Thermostable purified DNA-dependent DNA polymerases also efficiently catalyze RNA-dependent DNA pyrophosphorolysis on a RNA template at thermophilic temperatures, virtually also being reverse transcriptases or RNA-dependent DNA polymerases. Besides reverse tran-scription at thermophilic temperatures, they are advanta-geous that RT-PAP integrates RT step and PAP step into a single tube, and use Magnesium ion for high fidelity of amplification.

SUMMARY OF THE INVENTION

A thermophilic purified DNA-dependent DNA poly-merase was found to efficiently catalyze reverse transcrip-tion (RNA-dependent DNA polymerization) on a RNA template, virtually also being a reverse transcriptase (RNA-dependent DNA polymerase). The reverse transcriptase comprises an amino acid sequence which is more than 85% identical to any DNA-dependent DNA polymerase selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8.

The reverse transcriptase catalyzing reverse transcription on a RNA template comprises a DNA polymerase A domain which amino acid sequence is more than 90% identical to any DNA polymerase A domain selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8.

The reverse transcriptase catalyzing reverse transcription on a RNA template is a member of Type A family of DNA-dependent DNA polymerase.

The reverse transcriptase activity is inactivated at a tem-perature ≥83° C. when catalyzing reverse transcription on a RNA template.

The reverse transcriptase activity is inactivated at a tem-perature from 83° C. to 95° C. when catalyzing reverse transcription on a RNA template.

The reverse transcriptase catalyzes reverse transcription at a temperature from 55° C. to 70° C.

The reverse transcriptase catalyzes reverse transcription at an optimal temperature from 60° C. to 62° C.

The reverse transcriptase catalyzes reverse transcription on a RNA template to generate a reverse-transcribed DNA, and then a second DNA polymerase catalyzes DNA-depen-dent DNA polymerization using the reverse-transcribed DNA as template.

A thermophilic purified DNA-dependent DNA poly-merase catalyzes RNA-dependent DNA pyrophosphorolysis on a RNA template, virtually also being a reverse tran-scriptase (RNA-dependent DNA polymerase). The reverse transcriptase comprises an amino acid sequence which is more than 85% identical to any DNA-dependent DNA polymerase selected from the group consisting of SEQ ID NO: 5, SEQ ID NO: 6, SEQ ID NO: 7 and SEQ ID NO: 8.

The reverse transcriptase catalyzing RNA-dependent DNA pyrophosphorolysis on a RNA template comprises a DNA polymerase A domain amino acid sequence which is more than 90% identical to any DNA polymerase A domain selected from the group consisting of SEQ ID NO: 5, SEQ ID NO: 6, SEQ ID NO: 7 and SEQ ID NO: 8.

The reverse transcriptase catalyzing RNA-dependent DNA pyrophosphorolysis on a RNA template contains a phenylalanine to tyrosine substitution (Phe665Try or Phe420Try) of ID NO: 5, SEQ ID NO: 6, SEQ ID NO: 7 or SEQ ID NO: 8 corresponding to the wild-type counterpart sequence of SEQ ID NO: 1, SEQ ID NO: 2, SEQ ID NO: 3 or SEQ ID NO: 4.

The reverse transcriptase catalyzing RNA-dependent DNA pyrophosphorolysis on a RNA template is a member of Type A family of DNA-dependent DNA polymerase.

When a 3' blocked primer that has a non-extendable nucleotide at the 3' end (3' blocker) anneals to its RNA template, the reverse transcriptase catalyzes RNA-dependent DNA pyrophosphorolysis to remove the 3' blocker from the 3' blocked primer. Then the reverse transcriptase catalyzes reverse transcription on the same RNA template.

The reverse transcriptase activity is inactivated at a temperature ≥83° C. when catalyzing RNA-dependent DNA pyrophosphorolysis on a RNA template.

The reverse transcriptase activity is inactivated at a temperature from 83° C. to 95° C. when catalyzing RNA-dependent DNA pyrophosphorolysis on a RNA template.

The reverse transcriptase catalyzes RNA-dependent DNA pyrophosphorolysis at a temperature from 55° C. to 70° C.

The reverse transcriptase catalyzes RNA-dependent DNA pyrophosphorolysis at an optimal temperature from 60° C. to 62° C.

A method for reverse transcription (RNA-dependent DNA polymerization) comprises:

(a) a thermophilic purified DNA-dependent DNA polymerase catalyzing reverse transcription (RNA-dependent DNA polymerization) on a RNA template, also being reverse transcriptase (RNA-dependent DNA polymerase), comprises an amino acid sequence more than 85% identical to any DNA-dependent DNA polymerase selected from the group consisting of SEQ ID NO: 1, SEQ ID NO: 2, SEQ ID NO: 3, SEQ ID NO: 4, NO: 5, SEQ ID NO: 6, SEQ ID NO: 7 and SEQ ID NO: 8, and, (b) the reverse transcriptase catalyzes reverse transcription (RNA-dependent DNA polymerization) on a RNA template to generate a reverse-transcribed DNA.

Of the method for reverse transcription, the reverse transcriptase comprises a DNA polymerase A domain which amino acid sequence is more than 90% identical to any DNA polymerase A domain selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8.

Of the method for reverse transcription, the reverse transcriptase activity is inactivated at a temperature ≥83° C.

Of the method for reverse transcription, the reverse transcriptase activity is inactivated at a temperature from 83° C. to 95° C.

Of the method, the reverse transcriptase catalyzes reverse transcription at a temperature from 55° C. to 70° C.

Of the method, the reverse transcriptase catalyzes reverse transcription at an optimal temperature from 60° C. to 62° C.

The method for reverse transcription further comprises another step (c) a second DNA polymerase catalyzing DNA-dependent DNA polymerization using the reverse-transcribed DNA as template.

Of the method for reverse transcription, the steps (a) to (c) are conducted in a single reaction tube.

A method for RNA-dependent DNA pyrophosphorolysis comprises:

(a) a thermophilic purified DNA-dependent DNA polymerase catalyzing RNA-dependent DNA pyrophosphorolysis on a RNA template, also being reverse transcriptase (RNA-dependent DNA polymerase), comprises an amino acid sequence more than 85% identical to any DNA-dependent DNA polymerase selected from the group consisting of SEQ ID NO: 5, SEQ ID NO: 6, SEQ ID NO: 7 and SEQ ID NO: 8, (b) a 3' blocked primer that has a non-extendable nucleotide at the 3' end (3' blocker) anneals to a RNA template, and (c) the reverse transcriptase catalyzes RNA-dependent DNA pyrophosphorolysis to remove the 3' blocker from the 3' blocked primer.

Of the method for RNA-dependent DNA pyrophosphorolysis, the reverse transcriptase comprises a DNA polymerase A domain which amino acid sequence is more than 90% identical to any DNA polymerase A domain selected from the group consisting of SEQ ID NO: 5, SEQ ID NO: 6, SEQ ID NO: 7 and SEQ ID NO: 8.

Of the method for RNA-dependent DNA pyrophosphorolysis, the reverse transcriptase contains a phenylalanine to tyrosine substitution (Phe665Try or Phe420Try) corresponding to the wild-type counterpart sequence.

The method for RNA-dependent DNA pyrophosphorolysis further comprises step (d): the reverse transcriptase catalyzes reverse transcription on the RNA template to generate a reverse-transcribed DNA.

Of the method for RNA-dependent DNA pyrophosphorolysis, the reverse transcriptase activity is inactivated at a temperature ≥83° C.

Of the method for RNA-dependent DNA pyrophosphorolysis, the reverse transcriptase activity is inactivated at a temperature from 83° C. to 95° C.

Of the method, the reverse transcriptase catalyzes RNA-dependent DNA pyrophosphorolysis at a temperature from 55° C. to 70° C.

Of the method, the reverse transcriptase catalyzes RNA-dependent DNA pyrophosphorolysis at an optimal temperature from 60° C. to 62° C.

The method for RNA-dependent DNA pyrophosphorolysis further comprises:

(e) a second 3' blocked primer that has a non-extendable nucleotide at the 3' end (3' blocker) anneals to the reverse-transcribed DNA template, (f) a second DNA polymerase catalyzes DNA-dependent DNA pyrophosphorolysis to remove the 3' blocker from the 3' blocked primer to activate the primer, and (g) the second DNA polymerase catalyzes DNA-dependent DNA polymerization using the reverse-transcribed DNA as template.

Of the method for RNA-dependent DNA pyrophosphorolysis, the steps (a) to (g) are conducted in a single reaction tube.

DETAILED DESCRIPTION OF THE INVENTION

Terminology

Figure 1:
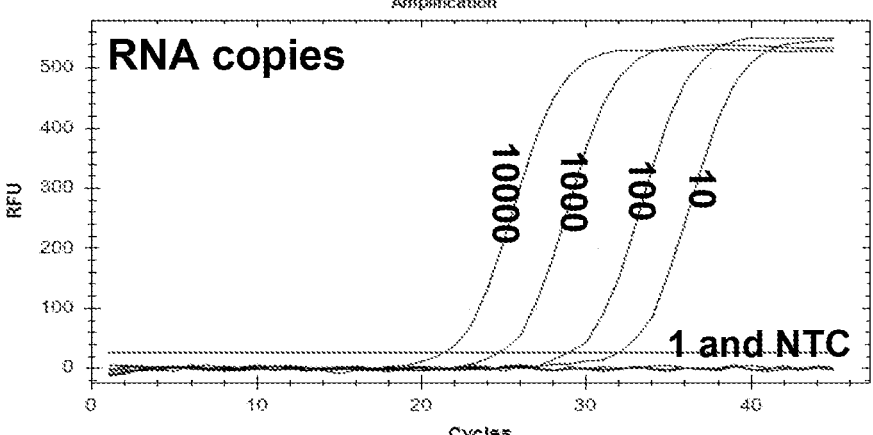
FIG. 1 shows RT-PAP assay V to detect COVID-19 viral RNA templates. To demonstrate the sensitivity, the amount of COVID-19 viral RNA was 10-fold serially diluted from 10,000 copies to a single digit of copies per reaction with 5 ng of reverse transcriptase Cpe-665Y used for reverse transcription step. X-axis is the cycle number and Y-axis is the net fluorescence signal in arbitrary units. Threshold line is also indicated. A linear relationship between the cope number of RNA template and its Ct value was set. In addition, non-template-controls showed no amplification signals, indicating the specificity.

Unless defined otherwise, all technical and scientific terms used herein have the same meaning as commonly understood by one of ordinary skill in the art.

Pyrophosphorolysis is the reverse reaction of deoxyribonucleic acid polymerization catalyzed by polymerase. In the presence of pyrophosphate, the 3' nucleotide is removed by a polymerase on duplex DNA to generate a triphosphate nucleotide and a 3' shortened duplex DNA (Deutscher and Kornberg, 1969):

$$[dNMP]_n + PPi \rightarrow [dNMP]_{n-1} + dNTP$$

DNA-dependent DNA pyrophosphorolysis refers to pyrophosphorolysis of DNA using a DNA template. It is the reverse reaction of DNA-dependent DNA polymerization RNA-dependent DNA pyrophosphorolysis refers to pyrophosphorolysis of DNA using a RNA template. It is the reverse reaction of RNA-dependent DNA polymerization.

3' blocked primer refers to a primer with a 3' non-extendable nucleotide (3' blocker), such as a dideoxynucleotide or an acyclonucleotide. The primer could not be directly extended from the 3' blocker, but it can be removed by pyrophosphorolysis and then the unblocked primer can be extended by polymerase. Besides 3' dideoxynucleotides as a blocker, other 3' blockers, such as acyclonucleotides that substitute a 2-hydroxyethoxymethyl group for the 2'-deoxyribofuranosyl sugar, are also used (Liu and Sommer, 2004a).

cDNA refers to a complementary DNA molecule synthesized on a RNA template.

Thermostable DNA polymerase (DNA-dependent or RNA-dependent) refers to a polymerase that is heat stable or heat resistant at ≥50° C.

Thermophilic DNA polymerase (DNA-dependent or RNA-dependent) refers to a polymerase with an optimal reaction temperature between 50° C. and 64° C.

Extreme thermophilic DNA polymerase (DNA-dependent or RNA-dependent) refers to a polymerase with an optimal reaction temperature between 65° C. and 80° C.

Hyperthermophilic DNA polymerase (DNA-dependent or RNA-dependent) refers to a polymerase with an optimal reaction temperature above 80° C.

DNA-dependent DNA polymerase refers to a polymerase characterized as catalyzing DNA polymerization or extension on a DNA template.

Reverse transcriptase or RNA-dependent DNA polymerase refers to a polymerase characterized as catalyzing DNA polymerization or extension on a RNA template.

Thermostable reverse transcriptase or RNA-dependent DNA polymerase refers to a reverse transcriptase that is heat stable or heat resistant at ≥50° C.

Thermophilic reverse transcriptase or RNA-dependent DNA polymerase refers to a reverse transcriptase with an optimal reaction temperature between 50° C. and 64° C.

Extreme thermophilic reverse transcriptase or RNA-dependent DNA polymerase refers to a reverse transcriptase with an optimal reaction temperature between 65° C. and 80° C.

Hyperthermophilic reverse transcriptase or RNA-dependent DNA polymerase refers to a reverse transcriptase with an optimal reaction temperature above 80° C.

Protein mutation refers to a change in amino acid residue at a location of a protein, like Cpe-665Y DNA polymerase. The change in amino acid residue is defined with respect to a naturally occurring protein such as Cpe DNA polymerase. A protein having a mutation is referred to as a "mutant" protein.

TaqFS is a mutant form of the wild-type Taq DNA polymerase containing F667Y amino acid changes compared with the wild-type DNA Taq sequence.

Cpe-665Y is a mutant form of Cpe DNA polymerase containing F665Y amino acid changes compared with the wild-type Cpe sequence.

A pair of primers means two opposing forward and reverse primers.

Singleplex-PAP means that one pair of primers amplify one template in a reaction.

Multiplex-PAP means that ≥2 pairs of primers amplify ≥2 potential templates in a reaction.

The 5' region of a primer is the 5' part of the primer sequence, such as the ten successive nucleotides from the 5' end.

The 3' region of a primer is the 3' part of the primer sequence, such as the ten successive nucleotides from the 3' end.

Central region of a primer is the middle part of the primer sequence between the 5' region and the 3' region.

Bidirectional-PAP (Bi-PAP) is a form of PAP that uses a pair of opposing blocked primers that overlap by one nucleotide at their 3' termini.

Exponential-PAP is a form of PAP that uses a pair of two opposing forward and reverse primers for exponential product accumulation with cycles. At least one primer is blocked primer.

Sensitivity or detection limit is defined as the smallest copy number of a template that generates a detectable product when the blocked primers match the template at the targeted nucleotide, such as the 3' end.

Specificity is defined as the largest copy number of a template that generates an undetectable product when the blocked primers mismatch the template at the targeted nucleotide, such as the 3' end.

Selectivity, the ratio of sensitivity to specificity, is defined as the ability to detect a small number of copies of the matched template in the presence of a large number of copies of mismatched templates without causing false positives.

Terminology of Bioinformatics

Alignment is the process or result of matching up the amino acid residues of two or more protein sequences to achieve the maximal level of identity.

Substitution is a non-identical amino acid at a given position in an alignment.

Identity is the extent to which two (nucleotide or amino acid) sequences have the same residues at the same positions in an alignment, often expressed as a percentage.

Similarity is the extent to which nucleotide or protein sequences are related. Similarity between two sequences can be expressed as a percent of sequence identity and/or a percent of positive substitutions.

Gap is a space introduced into an alignment to compensate for insertions and deletions in one sequence relative to another.

Terminology of Real-Time Fluorescence Detection

Baseline is the level of fluorescence signal during initial cycles. The low level can be considered as background or "noise" of the reaction.

Threshold is defined as the level of fluorescence signal that is a significant higher than baseline signal and can distinguish amplification signal from the background.

Ct (threshold cycle) is the cycle number at which the fluorescence signal crosses the threshold.

Amplification efficiency is defined as the percent of template that is amplified by the end of a cycle.

Terminology of Reverse Transcription

Reverse transcription efficiency is defined as the percent of RNA template that is reverse-transcribed by the end of reaction.

Reverse transcriptase activity is defined as the ability to polymerize deoxynucleoside triphosphates using a RNA template within a give period of time.

Reverse transcriptase specific activity is defined as the ratio of the activity to the amount of reverse transcriptase.

EXAMPLES

The practice of the present invention employs, unless otherwise indicated, common techniques of chemistry, molecular biology and recombinant DNA, e.g., those by Sambrook et al., Molecular Cloning, 2nd Ed. (Sambrook et al., 1989); Sambrook and Russell, Molecular Cloning, 3rd Ed. (Sambrook and Russell, 2001); Ausubel, Current Protocols in Molecular Biology (Ausubel, 1994).

Example 1

Purified Reverse Transcriptases

The present invention provides purified wild-type DNA-dependent DNA polymerases of Cpe, Cfe, Cis and Cpe-Del (SEQ ID NOS: 1-4) in full-length form or in N-terminal deletion form, which were sequenced previously in bacteria of *Carboxydothermus pertinax* (Accession: WP_075859958), *Carboxydothermus ferrireducens* (Accession: WP_034541897), *Carboxydothermus islandicus* (ACCESSION: WP_075865044) and *Carboxydothermus pertinax* (accession: WP_075859958), respectively.

The wild-type DNA-dependent DNA polymerases were identified as Type A DNA-dependent DNA polymerases by protein homology method with lengths of 831AA (amino acid), 831AA, 831AA and 584AA (SEQ ID NOS: 1-4), respectively. Among them, Cpe-Del (SEQ ID NO: 4) is a N-terminal deletion form in which the N-terminal 246AA are deleted from Cpe (SEQ ID NO: 1).

The present invention also provides purified mutant DNA-dependent DNA polymerases of Cpe-665Y, Cfe-665Y, Cis-665Y and Cpe-Del-420Y (SEQ ID 5-8) in full-length form or in N-terminal deletion form, which contain F665Y (Phe665Try), F665Y, F665Y and F420Y substitutions corresponding to their wild-type counterpart sequences (SEQ ID NOS: 1-4). We designed this Phenylalanine to Tyrosine substitution and expected it to increase the efficiency of RNA-dependent DNA pyrophosphorolysis to remove the 3' blocker from a 3' blocked primer compared with their wild-type counterparts.

The mutant DNA-dependent DNA polymerases were also identified as Type A DNA-dependent DNA polymerases by protein homology method with lengths of 831AA, 831AA, 831AA and 584AA (SEQ ID NOS: 5-8), respectively. Among them, Cpe-Del-420Y (SEQ ID NO: 8) is a N-terminal deletion form in which the N-terminal 246AA are deleted compared to Cpe-665Y with 831AA length (SEQ ID NO: 5).

Besides DNA-dependent DNA polymerization, the purified wild-type and mutant DNA-dependent DNA polymerases were found to efficiently catalyze reverse transcription (RNA-dependent DNA polymerization) using RNA templates at thermophilic temperatures, thus also being reverse transcriptases (RNA-dependent DNA polymerases) in nature (EXAMPLES 3-6). These genes were cloned with the proteins expressed and purified for the purpose of reverse transcription for RT-PCR.

Furthermore, besides DNA-dependent DNA polymerization and reverse transcription, the mutant DNA polymerases which contain phenylalanine to tyrosine substitutions (SEQ ID NOS: 5-8) were found to efficiently catalyze RNA-dependent DNA pyrophosphorolysis to remove the 3' blocker, such as a 3' dideoxynucleotide, from a 3' blocked primer on a RNA template at thermophilic temperatures, thus being reverse transcriptases again (RNA-dependent DNA polymerases) (EXAMPLES 3-6). These genes were cloned with the proteins expressed and purified for the purpose of RT-PAP to catalyze RNA-dependent DNA pyrophosphorolysis.

Comparison of Amino Acid Sequences Among the Reverse Transcriptases

Amino acid sequences of the above DNA polymerases (reverse transcriptases or RNA-dependent DNA polymerases) were aligned to explore conserved regions, which we assume to have functional importance. Specifically, BLAST (basic local alignment search tool) was used to compare each two amino acid sequences among the DNA polymerases.

In the alignment, the amino acid residues of each two DNA polymerase sequences were aligned to achieve the maximal level of identity. The identity, defined as the extent to which two DNA polymerase amino acid sequences have the same residues at the same positions, was searched and expressed as a percentage among each two of the wild-type DNA polymerases of Cpe, Cfe, Cis and Cpe-Del (SEQ ID NOS: 1-4) (Table 1) and among each two of the mutant DNA polymerases of Cpe, Cfe, Cis and Cpe-Del (SEQ ID NOS: 5-8) (Table 2).

For example, 831 amino acids were aligned between Cpe and Cfe DNA polymerase sequences, and 723 of the 831 amino acids, or 87.00%, were found identical at the same positions. The minimum identity was aligned to be 85.10%, which is between Cpe-del and Cis polymerase sequences among the wild-type DNA polymerases (Table 1) or between Cpe-del-420Y and Cis665Y polymerase sequences among the mutant DNA polymerases (Table 2), suggesting that as low as 85.10% of identity or conservation level does not affect the DNA polymerase (reverse transcriptases or RNA-dependent DNA polymerases) functions substantially.

The gap, defined as one or more amino acid residues deleted or inserted between each two polymerase amino acid sequences was also searched and expressed as a percentage among each two of the wild-type DNA polymerases of Cpe, Cfe, Cis and Cpe-Del (SEQ ID NOS: 1-4) and among each two of the mutant DNA polymerases of Cpe-665Y, Cfe-665Y, Cis-665Y and Cpe-Del-420Y (SEQ ID NOS: 5-8).

No gaps (0%) were found between each two DNA polymerase sequences among the wild-type polymerases or among the mutant DNA polymerases. For example, between Cpe and Cfe DNA polymerase sequences, 831 amino acids were aligned, and zero of the 831 amino acid residues, or 0%, were found deleted or inserted, suggesting that a gap is likely to affect the DNA polymerase (reverse transcriptases or RNA-dependent DNA polymerases) functions substantially.

To confirm the above findings of alignments, experiments were conducted in EXAMPLES 3-6. Although as low as 85% of identity among their amino acid sequences (Tables 1 and 2), the DNA polymerases showed the activities to catalyze reverse transcription (RNA-dependent DNA polymerization) and RNA-dependent DNA pyrophosphorolysis Furthermore, although the N-terminal 246AA was deleted form its full-length form, the DNA polymerase of Cpe-Del or Cpe-Del-420Y still kept the activities for reverse transcription and RNA-dependent DNA pyrophosphorolysis, showing that the N-terminal regions are not essential for the activities (EXAMPLES 3-6).

TABLE 1

| Amino acid identities among the wild-type DNA polymerases | | | | |
|---|---|---|---|---|
| | | SEQ ID | | |
| Polymerase | NO: 1 Cpe | NO: 2 Cfe | NO: 3 Cis | NO: 4 Cpe-Del |
| NO: 1 Cpe | | | | |
| NO: 2 Cfe | 87.00%, 723/831 [a] | | | |
| NO: 3 Cis | 85.80%, 713/831 | 94.83%, 788/831 | | |
| NO: 4 Cpe-del | 100%, 584/584 | 86.82%, 507/584 | 85.10%, 497/584 | |

Footnotes of Table 1.
[a] 831 amino acids were aligned between Cpe and Cfe DNA polymerase sequences. 723 of the 831 amino acids, or 87.00%, were found identical at the same positions.

TABLE 2

| Amino acid identities among the mutant DNA polymerases | | | | |
|---|---|---|---|---|
| | | SEQ ID | | |
| SEQ ID | Polymerase | NO: 5 Cpe-665Y | NO: 6 Cfe-665Y | NO: 7 Cis-665Y | NO: 8 Cpe-Del-420Y |
| NO: 5 | Cpe-665Y | | | | |
| NO: 6 | Cfe-665Y | 87.00%, 723/831 | | | |
| NO: 7 | Cis-665Y | 85.80%, 713/831 | 94.83%, 788/831 | | |
| NO: 8 | Cpe-Del-420Y | 100%, 584/584 | 86.82%, 507/584 | 85.10%, 497/584 | |

On the other hand, we identified functional domains of each DNA polymerase (reverse transcriptase or RNA-dependent DNA polymerase) including 1) a 5'-3' exonuclease domain (a total of 259 amino acids from the 2nd to the 260th amino acid of the 831 amino acid sequence), and 2) a DNA polymerase A domain which sustains the activity for polymerization (a total of 373 amino acids from the 452nd to the 824th amino acid of the 831 amino acid sequence) by protein homology method with *E. coli* DNA polymerase A.

The identity of the DNA polymerase A domains was expressed as a percentage among each two of the wild-type DNA polymerases of Cpe, Cfe, Cis and Cpe-Del (SEQ ID NOS: 1-4) (Table 3) and among each two of the mutant DNA polymerases of Cpe, Cfe, Cis and Cpe-Del (SEQ ID NOS: 5-8) (Table 4).

For example, the 373 amino acids of the DNA polymerase A domains were aligned between Cpe and Cfe DNA polymerase sequences, and 341 of the 373 amino acids, or 91.42%, were found identical at the same positions. The minimum identity was aligned to be 90.35%, which is between Cpe or Cpe-del and Cis DNA polymerase sequences among the wild-type DNA polymerases (Table 3) or between Cpe-665Y or Cpe-del-420Y and Cis665Y polymerase sequences among the mutant DNA polymerases (Table 4), suggesting that as low as 90.35% of identity or conservation level does not affect the DNA polymerase activities substantially.

The gap between each two amino acid sequences of the DNA polymerase A domains was also expressed as a percentage among each two of the wild-type DNA polymerases of Cpe, Cfe, Cis and Cpe-Del (SEQ ID NOS: 1-4) and among each two of the mutant DNA polymerases of Cpe-665Y, Cfe-665Y, Cis-665Y and Cpe-Del-420Y (SEQ ID NOS: 5-8).

No gaps (0%) were found between each two DNA polymerase A domains. For example, between Cpe and Cfe DNA polymerase sequences, 373 amino acids were aligned, and zero of the 373 amino acid residues, or 0%, were found deleted or inserted, suggesting that a gap is likely to affect the DNA polymerase activities substantially.

Besides the alignments of DNA polymerase A domains, the importance of these domains was also demonstrated in EXAMPLES 3-6. Although as low as 90% of identity among their DNA polymerase A domains (Tables 3 and 4), the DNA polymerases showed RNA-dependent DNA polymerase (reverse transcriptase) activities to catalyze reverse transcription (RNA-dependent DNA polymerization) and RNA-dependent DNA pyrophosphorolysis.

Furthermore, after Cpe-Del (SEQ ID NO: 4) and Cpe-Del-420Y (SEQ ID NO: 8) have deleted their 5'-3' exonuclease domains, they still sustained their activities of reverse transcription and RNA-dependent DNA pyrophosphorolysis, showing again that their 5'-3' exonuclease domains play unessential roles and their DNA polymerase A domains play essential roles in their activities for reverse transcription and RNA-dependent pyrophosphorolysis (EXAMPLES 3-6).

TABLE 3

| Amino acid identities among the DNA polymerase A domains of the wild-type DNA polymerases | | | | |
|---|---|---|---|---|
| | | SEQ ID | | |
| Polymerase | NO: 1 Cpe | NO: 2 Cfe | NO: 3 Cis | NO: 4 Cpe-Del |
| NO: 1 Cpe | | | | |
| NO: 2 Cfe | 91.42%, 341/373 [a] | | | |
| NO: 3 Cis | 90.35%, 337/373 | 96.51%, 360/373 | | |

TABLE 3-continued

Amino acid identities among the DNA polymerase A
domains of the wild-type DNA polymerases

| | | SEQ ID | | |
| | | | | |
| Polymerase | NO: 1 Cpe | NO: 2 Cfe | NO: 3 Cis | NO: 4 Cpe-Del |
|---|---|---|---|---|
| NO: 4 Cpe-del | 100%, 373/373 | 91.42%, 341/373 | 90.35%, 337/373 | |

Footnotes of Table 3.
*a* 373 amino acids were aligned between Cpe and Cfe DNA polymerase sequences. 341 of the 373 amino acids, or 91.42%, were found identical at the same positions.

TABLE 4

Amino acid identities among the DNA polymerase A
domains of the mutant DNA polymerases

| | | SEQ ID | | | |
| | | | | NO: 7 | NO: 8 |
| | | NO: 5 | NO: 6 | Cis- | Cpe-Del- |
| SEQ ID | Polymerase | Cpe-665Y | Cfe-665Y | 665Y | 420Y |
|---|---|---|---|---|---|
| NO: 5 | Cpe-665Y | | | | |
| NO: 6 | Cfe-665Y | 91.42%, 341/373 | | | |
| NO: 7 | Cis-665Y | 90.35%, 337/373 | 96.51%, 360/373 | | |
| NO: 8 | Cpe-Del-420Y | 100%, 373/373 | 91.42%, 341/373 | 90.35% 337/373 | |

Example 2

Construction of Recombinant Plasmids

The present invention provides nucleic acid sequences encoding the wild-type DNA polymerases (reverse transcriptases) (SEQ ID NOS: 9-12). They are also available from GenBank of Cpe: Accession: NZ_BDJK01000055, Region: 138926 . . . 141421; Cfe: Accession: NZ_A-TYG01000019, Region: 19948 . . . 22443; Cis: Accession: NZ_BDJL01000019, Region: 39893 . . . 42388; Cpe-Del: Accession: NZ_BDJK01000055, Region: 139664 . . . 141421. It also provides nucleic acid sequences encoding the mutant reverse transcriptases (SEQ ID NOS: 13-16), in each of which an amino acid is substituted to contain F665Y, F665Y, F665Y and F420Y, respectively.

A wild-type or mutant DNA polymerase gene of a pair was chosen (SEQ ID NOS: 1-8). The nucleic acid codons of the gene were optimized for a high level of expression in *E. coli* cells, and then its DNA sequence was chemically synthesized with adapters at each end (GenScript Biotech). To construct a recombinant plasmid, the DNA sequence was then ligated into pET vector DNA at the Nde I and BamH I restriction sites according to Navagen pET system user manual. For convenient purification, the expressed polymerase contained 6× or 10×His-Tag at the N-terminus or C-terminus (Table 5).

The counterpart recombinant plasmid DNA of the pair was constructed by site-directed mutagenesis method with QuikChange lightning site-directed mutagenesis kit according to Agilent's user manual so that a substitution change was introduced into the polymerase gene (Table 5).

Then each recombinant plasmid DNA transformed DH5α *E. coli* cells and its plasmid DNA was extracted from *E. coli* colonies. The DNA sequence of the gene was sequenced by ABI Sanger sequencing.

Expression of the Reverse Transcriptases

Each cloned polymerase was expressed in transformed T7 Express lysY/1*q E. coli* cells according to BioLabs' manual, including steps: 1) transformation of *E. coli* cells, 2) a small volume of LB culture of *E. coli* colonies, 3) a large volume of LB culture of the *E. coli* cells, 4) IPTG induction of protein expression in the *E. coli* cells, and 5) collection of the cultured *E. coli* cells by centrifuge

TABLE 5

Characteristics of the constructed recombinant plasmids

| Inserted polymerase gene | Vector | Bacteria and expression | Tag for purification |
|---|---|---|---|
| Cpe, Cpe-665Y: SEQ ID NOS: 1, 5 | pET-16b, between Nde I and BamH I restriction sites | *E.coli*, T7 Express system | 10X Histidines at N-terminal region |
| Cfe, Cfe-665Y: SEQ ID NOS: 2, 6 | pET-16b, between Nde I and BamH I restriction sites | *E.coli*, T7 Express system | 10X Histidines at N-terminal region |
| Cis, Cis-665Y: SEQ ID NOS: 3, 7 | pET-20b, between Nde I and BamH I restriction sites | *E.coli*, T7 Express system | 6X Histidines at C-terminal region |
| Cpe-Del, Cpe-Del-665Y *a*: SEQ ID NOS: 4, 8 | pET-14b, between Nde I and BamH I restriction sites | *E.coli*, T7 Express system | 6X Histidines at N-terminal region |

Footnotes of Table 5.
*a* Six nucleotides of 5′ ATGGGC3′ coding Methionine and Glycine amino acids at the N-terminus was added to the 5′ end of the gene sequence for convenient expression.

Purification of the Reverse Transcriptases

Because an expressed polymerase contained 6× or 10×His-Tags at the N-terminus or C-terminus, His-Tag affinity chromatography was chosen for the DNA polymerase purification. A HisTrap HP column was used under native conditions with an AKTA RFLP instrument according to manufacturer's instruction (GE lifesciences).

Within the HisTrap HP column, the chelating group, attached to agarose beads, is pre-charged with nickel ion, which selectively binds the histidine-Tag polymerase. Then 250 mM Imidazole elutes the bound polymerase through competitive binding.

The purification procedure included four basic steps: 1) cell lysis, 2) polymerase binding to the HisTrap HP column, 3) washing and 4) step-elution. Two buffers A and B were used: A buffer contained 50 mM $KH_2PO_4/K_2HPO_4$, pH 8.0, 300 mM NaCl, 10 mM Imidazole used for steps 1) to 3), and B buffer contained 50 mM $KH_2PO_4/K_2HPO_4$, pH 8.0, 300 mM NaCl, 250 mM Imidazole used for step 4). Then the eluted polymerase was concentrated by centrifuging through a Millipore Amicon Ultra 10K ultra-filtration column.

A typical yield of the eluted polymerase was 4-20 mg from 1000 ml of *E. coli* culture. The purified polymerase showed one major band on SDS-PAGE gel after Coomassie Blue staining, indicating ≥90% purity. Based on the gel mobility, the major band was estimated 95,000 Daltons for a full-length polymerase and 67,000 Daltons for a deleted polymerase.

The purified polymerase was stored at 1 mg per mL of storage buffer, containing 20 mM Tris-HCl (pH 8.0 at 25° C.), 100 mM KCl, 0.1 mM EDTA, 1 mM DTT, 0.2% Tween-20 and 50% Glycerol at −20° C.

Example 3

Preparation of Primers

Each 3′ blocked primer, blocked with ddCMP at the 3′ end, was chemically synthesized and HPLC purified by Integrated DNA Technologies. The regular DNA primers were also synthesized by the same vendor (Table 6).

the reverse transcriptase, 1.6 U of Taq DNA polymerase and 0.2 ng of total RNA template. For RT-PCR, the RT step

TABLE 6

List of primers and assays

| Assay | Name [b] | Sequence (5' to 3') (SEQ ID NO:) | Location | Product size (bp) | Starting template |
|---|---|---|---|---|---|
| I. RT-PCR [a] | ACTB(426)25D | CAACCGCGAGAAGATGA CCCAGATC (17) | Exons 3 and 4 | 63 | Total RNA |
| | ACTB(488)25U | GCAACGTACATGGCTGG GGTGTTGA (18) | Exon 4 | | |
| II. RT-PCR | ACTB(426)25D | CAACCGCGAGAAGATGA CCCAGATC (19) | Exons 3 and 4 | 280 | Total RNA |
| | ACTB(705)25U | TTCCCGCTCGGCCGTGGT GGTGAAG (20) | Exon 4 | | |
| III. RT-PAP | ACTB(426)25D | CAACCGCGAGAAGATGA CCCAGATC (21) | Exons 3 and 4 | 63 | Total RNA |
| | ACTB(488)30U | GCAACGTACATGGCTGG GGTGTTGAAGGTddC (22) [c] | Exon 4 | | |
| IV. RT-PAP | ACTB(426)25D | CAACCGCGAGAAGATGA CCCAGATC (23) | Exons 3 and 4 | 147 | Total RNA |
| | ACTB(572)30U | ACAGTGTGGGTGACCCC GTCACCGGAGTCddC (24) | Exon 4 | | |
| V. RT-PAP | COVID-19(28679)28D | GAGGGAGCCTTGAATAC ACCAAAAGATddC (25) | N region | 76 | Clinical RNA sample |
| | COVID-19(28754)28U | GTTGTAGCACGATTGCAG CATTGTTAGddC (26) | N region | | |
| VI. RT-PAP | ACTB(434)28D | AGAAGATGACCCAGATC ATGTTTGAGAddC (27) | Exons 3 and 4 | 80 | Clinical RNA sample |
| | ACTB(512)27U | TTACAGGGATAGCACAG CCTGGATAGddC (28) | Exon 4 | | |

Footnoots of Table 6.
[a] In order to avoid non-specific amplification from potentially contaminated genomic DNA, RT-PCR and RT-PAP primers were designed to anneal to regions that span introns of the human ACTB gene.
[b] For example, ACTB means the human ACTB gene; (426), 5' end of the primer begins at nucleotide 426; D, downstream (i.e., in the direction of transcription). The ACTB mRNA is from GenBank accession: NM_001101.3. The COVID-19 viral RNA is from GenBank accession: MN908947.
[c] Due to the availability of chemical synthesis, ddCMP was exampled.

Total RNA Extraction

The total RNA was extracted from human blood white cells using QIAamp RNA kit according to Qiagen' protocol (QIAamp RNA Blood Mini Handbook). Within the process, RNase-Free DNase was used to remove contaminated genomic DNA. The concentration of the total RNA was measured by a spectrophotometer at 260 nm. It was stored at −20° C. until use.

Clinical RNA Sample Extraction

Clinical COVID-19 positive and negative samples were collected from nasopharyngeal or oropharyngeal swabs from the upper respiratory system. The RNA of a sample was extracted using QIAamp Viral RNA Mini Kits (Qiagen) following the manufacturers' instructions. The starting volume of the sample was 200 μL and the elution volume was 50 μL. Besides the COVID-19 viral RNA, the eluted sample contained co-extracted human RNA. The quantity of the extracted sample was measured by a EUA approved COVID-19 viral RNA diagnostic RT-PCR kit. It was stored at −20° C. until use.

RT-PCR to Measure Reverse Transcriptase Activity

Unless stated otherwise, the RT-PCR reaction mixture of 20 μl contained 50 mM Tris-HCl (pH 8.8 at 25° C.), 10 mM $(NH_4)_2SO_4$, 1.5 mM $MgCl_2$, 200 μM each dNTPs (dATP, dTTP, dGTP and dCTP), 0.1-0.15 μM each primer of Assay I or II, 0.1×SybrGreen I dye, 0.02% Twee-20, 5-200 ng of (reverse transcription) and the PCR step (DNA-dependent DNA polymerization) were integrated into a single reaction tube.

A Bio-Rad CFX96 real time PCR detection system was used for quantification of the amplified product. Analysis mode: SybrGreen fluorophore, Baseline setting: baseline subtracted curve fit, Threshold cycle (Ct) determination: single threshold, Baseline method: SYBR auto calculated, Threshold setting: auto calculated.

For RT-PCR Assays I and II, the program entailed 60° C. for 10 minutes for reverse transcription; then 95° C. for 2 minutes for heat-inactivation of reverse transcriptase activity; and then cycling 95° C. for 10 seconds, 60° C. for 30 seconds, 72° C. for 1 minute for 35 cycles. To confirm the amplified product, melting curve analysis was followed from 72° C. to 95° C. with increment 1° C. and holding 5 seconds.

RT-PAP to Measure Reverse Transcriptase Activity

Unless stated otherwise, the PAP reaction mixture of 20 μl contained 50 mM Tris-HCl (pH 8.0 at 25° C.), 10 mM $(NH_4)_2SO_4$, 1.0-1.2 mM $MgCl_2$, 25 μM each dNTPs (dATP, dTTP, dGTP and dCTP), 0.10-0.15 μM each primer of Assay III, IV, V or VI, 90 μM $Na_4PP_i$, 0.1×SybrGreen I dye, 0.02% Twee-20, 5-200 ng of the reverse transcriptase, 1.6 U of TaqFS DNA polymerase and 0.2 ng of total RNA template or 5 μl of COVID-19 viral RNA sample. For RT-PAP, the RT step (RNA-dependent DNA pyrophosphorolysis and reverse transcription) and the PAP step (DNA-dependent DNA pyrophosphorolysis and DNA-dependent DNA polymerization) were integrated into a single reaction tube.

A Bio-Rad CFX96 real time PCR detection system was used for quantification of the amplified product. Analysis mode: SybrGreen fluorophore, Baseline setting: baseline subtracted curve fit, Threshold cycle (Ct) determination: single threshold, Baseline method: SYBR auto calculated, Threshold setting: auto calculated.

For RT-PAP Assays III and IV, the program entailed 60° C. for 10 minutes for reverse transcription; then 95° C. for 2 minutes for heat-inactivation of reverse transcriptase activity; and then cycling 95° C. for 10 seconds, 60° C. for 30 seconds, 72° C. for 1 minute for 35 cycles. To confirm the amplified product, melting curve analysis was followed from 72° C. to 95° C. with increment 1° C. and holding 5 seconds.

For RT-PAP Assays V and IV, the program entailed 60° C. for 10 minutes for reverse transcription; 95° C. for 2 minutes for heat-inactivation of reverse transcriptase activity; and then cycling 95° C. for 10 seconds, 64° C. for 1 minute for 45 cycles. To confirm the amplified product, melting curve analysis was followed from 64° C. to 95° C. with increment 1° C. and holding 5 seconds to confirm the amplified product.

Example 4

RT-PCR

RT-PCR includes two steps: 1) reverse transcription of a RNA template to produce a cDNA catalyzed by a reverse transcriptase, and 2) PCR amplification of the cDNA as template catalyzed by a DNA-dependent DNA polymerase, preferably in the same single reaction tube. Reverse transcription is considered as the efficiency limit of the two-step process.

The eight wild-type and mutant DNA polymerases (reverse transcriptases or RNA-dependent DNA polymerases) of Cpe, Cfe, Cis and Cpe-Del (SEQ ID NOS: 1-4) as well as Cpe-665Y, Cfe-665Y, Cis-665Y and Cpe-Del-420Y (SEQ ID NOS: 5-8) were tested for reverse transcription in RT-PCR.

We designed two RT-PCR Assays I and II (Table 6). RT-PCR Assay I amplifies a 63-bp ACTB mRNA template with primers ACTB(426)25D and ACTB(488)25U (SEQ ID NOS: 17 and 18), and Assay II amplifies a 280-bp ACTB mRNA template with primers ACTB(426)25D and ACTB (705)25U (SEQ ID NOS: 19 and 20). Each assay has a forward primer and a reverse primer with the reverse primer matching the RNA template.

Unless stated otherwise, the reaction composition and thermocycling program are described in EXAMPLE 3. Heat-Inactivation Initially we found that when a denaturing step at 94° C. or 95° C. for 2 minutes was added before reverse transcription step, any wild-type or mutant reverse transcriptase could not amplify RNA templates, demonstrating that the reverse transcriptase could not tolerate 94° C. or a higher temperature even for a short period of time.

To test the heat-inactivation in detail, we examined the effect of various temperatures on the reverse transcriptases. In a special program, gradient temperatures from 83° C. to 94° C. for 2 minutes were added before the reverse transcription step.

With RT-PCR Assay I, after heated at 83° C. for 2 minutes, a little amplification signal (±), indicated by a much delayed Ct value and a much lower RFU (relative fluorescent unit), was observed, estimating that >90% of reverse transcriptase activity was inactivated (Left part of Table 7). With RT-PCR Assay II, no amplification signal was found after heated at 83° C. for 2 minutes. This difference is because the product size of RT-PCR Assay II is 280-bp, much larger than 63-bp of RT-PCR Assay I. When at 85° C. or higher temperatures, no amplification signals were observed with both RT-PCR Assays I and II, estimating that >99% of reverse transcriptase activities were inactivated (Left part of Table 7).

The reverse transcriptases showed similar properties of heat-inactivation, although as low as 85% of identity among their amino acid sequences (Tables 1 and 2) and as low as 90% of identity among their DNA polymerase A domains (Tables 3 and 4).

In addition, no-template-control or no-reverse-transcriptase-control did not show amplifications, indicating the specificity.

This heat-activation is useful to RT-PCR because it prevents the RT step from interacting with the PCR step when they are integrated into a single tube.

TABLE 7

Remaining reverse transcriptase activities after heat-activation

| | Amplification signal and estimated remaining activity | | | |
|---|---|---|---|---|
| Heat temperature | RT-PCR assay I [a] | RT-PCR assay II [a] | RT-PAP assay III [c] | RT-PAP assay IV [c] |
| 94.0° C. | −, NA [b] | −, NA | −, NA [a] | −, NA |
| 90.0° C. | −, NA | −, NA | −, NA | −, NA |
| 87.4° C. | −, NA | −, NA | −, NA | −, NA |
| 85.3° C. | −, NA | −, NA | −, NA | −, NA |
| 83.0° C. | +/−, 5-10% | −, NA | +/−, 5-10% | −, NA |

Footnotes of Table 7
[a] In the left part, with RT-PCR assays I and II, 5 ng and 10 ng of Cfe polymerase was added to a 20 ul of reaction, respectively.
[b] Amplification signals can be divided into five levels of +++, ++, +, +/− and −. +/− means very weak amplification and − means no amplification initiated by the reverse transcriptases. The remaining activity was estimated from the amplification signal, indicated by its Ct value and RFU (relative fluorescent unit). NA means not available due to too low level of the remaining activity, such as <1%.
[c] In the right part, with RT-PAP assays III and IV, 5 ng and 10 ng of Cfe-665Y polymerase was added to a 20 ul of reaction, respectively (EXAMPLE V).

Optimal Temperatures

To test optimal temperatures, we examined the effect of various reaction temperatures. A special program entailed gradient temperatures from 56° C. to 66.5° C. for 10 minutes for reverse transcription step.

RT-PCR Assay II is a larger and more difficult target for reverse transcription, and thus it reflects the optimal temperatures more accurately than RT-PCR Assay I.

With RT-PCR Assay II, each reverse transcriptase was tested to measure Ct values at different temperatures (Left part of Table 8). Because Ct values are directly proportional to the reverse transcriptase activities or efficiencies, the Ct values can represent the reverse transcriptase activities or efficiencies. For comparison of the Ct values at the different temperatures, a ΔCt is set which equals to a Ct value subtracts that at 60.1° C. (Left part of Table 8). The results showed that the reverse transcriptases catalyzed reverse transcription in the RT-PCR assays substantially from 56° C. to 66.5° C. (Left part of Table 8). At 60.1-62.7° C., the Ct values were earliest and the ΔCt values were the smallest, indicating the reverse transcription activities or efficiencies to be highest at 60.1-62.7° C.

In addition, other tests showed that the reverse transcriptases still had observable activities at 55° C. and at 70° C.

Furthermore, no-template-control or no-reverse-transcriptase-control did not show amplifications, indicating the specificity.

The reverse transcriptases showed similar results of optimal temperatures, although as low as 85% of identity among their amino acid sequences (Tables 1 and 2) and as low as 90% of identity among their DNA polymerase A domains (Tables 3 and 4).

TABLE 8

Optimal temperatures of reverse transcription

| RT reaction | RT-PCR assay II | | RT-PAP assay IV | |
| --- | --- | --- | --- | --- |
| temperature | $Ct^a$ | $\Delta Ct$ to 60.1° C.[b] | $Ct^c$ | $\Delta Ct$ to 60.1° C. |
| 66.5° C. | 25.6 | 3.5 | 22.6 | 2.3 |
| 65.9° C. | 25.0 | 2.9 | 22.0 | 1.7 |
| 64.8° C. | 23.3 | 1.2 | 21.1 | 0.8 |
| 62.7° C. | 22.2 | 0.1 | 20.2 | −0.1 |
| 60.1° C. | 22.1 | 0 | 20.3 | 0 |
| 58.1° C. | 23.0 | 0.9 | 21.4 | 1.1 |
| 56.7° C. | 24.2 | 2.1 | 22.4 | 2.1 |
| 56.0° C. | 25.8 | 3.7 | 23.2 | 2.9 |

Footnotes of Table 8.

[a] In the left part with RT-PCR assay II, a Ct value was obtained when 10 ng of Cfe DNA polymerase was added to a 20 ul of reaction.

[b] For comparison of the Ct values at the various temperatures more conveniently, a ΔCt is set which equals to a Ct value subtracts that at 60.1° C.

[c] In the left part with RT-PAP assay IV, a Ct value was obtained when 5 ng of Cfe-665Y DNA polymerase was added to a 20 ul of reaction (EXAMPLE V).

Specific Activity

In order to compare relative activities for reverse transcription among the reverse transcriptases, a term of specific activity is introduced which is defined as the minimum amount (ng) of a reverse transcriptase that has an almost 100% efficiency in reverse transcription step.

RT-PCR Assay II was chosen because it is a larger and more difficult target and can measure the level of reverse transcriptase activity more obviously than RT-PCR Assay I.

We tested and compared the specific activities of the reverse transcriptases. The amount of each reverse transcriptase was 2-fold serially diluted from up to 200 ng to 1 ng in 20 µl of reaction. The Ct value was determined to estimate the minimum amount of the reverse transcriptase which has an almost 100% efficiency in the reverse transcription step. For comparison of the relative activities among the reverse transcriptases, the ratio of the minimum amount of a reverse transcriptase to that of Cpe was calculated (Left part of Table 9). The reverse transcriptases showed various specific activities with Cpe DNA polymerase having the highest specific activity among them.

In melting curve analysis, only one melting peak showed the $T_m$ value to be 88° C. of the amplified product in RT-PAR Assay II. No-template-control or no-reverse-transcriptase-control did not show any measurable Ct, showing specificity of the amplification.

In addition, when RT-PCR Assay I was used, the specific activities were higher with less amounts of the reverse transcriptases required than those in RT-PCR Assay II.

The reverse transcriptases showed various specific activities with the particular reverse transcriptases and with the particular RT-PCT assays.

TABLE 9

Specific activities of the reverse transcriptases

| | RT-PCR Assay II | | | RT-PAP Assay IV | |
| --- | --- | --- | --- | --- | --- |
| Polymerase | The minimum amount[a] | Ratio to Cpe[b] | Polymerase | The minimum amount[a] | Ratio to Cpe-665Y[b] |
| Cpe | 10 ng | 1 | Cpe-665Y | 5 ng | 1 |
| Cfe | 20 ng | 2 | Cfe-665Y | 10 ng | 2 |
| Cis | 80 ng | 8 | Cis-665Y | 40 ng | 8 |
| Cpe-Del | 60 ng | 6 | Cpe-Del-665Y | 20 ng | 4 |

Footnotes of Table 9.

[a] The amount of a reverse transcriptase was 2-fold serially diluted from 160 ng to 1.25 ng in 20 µl of reaction and incubated at 60° C. for 10 minutes in reverse transcription step. The Ct value was determined with the minimum amount of the reverse transcriptase estimated. The minimum amount of a reverse transcriptase is defined to have a Ct value of an almost 100% efficiency of reverse transcription.

[b] For comparison of the specificity activities among the reverse transcriptases, the ratio of the minimum amount of a reverse transcriptase to that of Cpe or Cpe-665Y is set.

Example 5

RT-PAP

RT-PAP includes two steps of RT and PAP. 1) Using a RNA template, a reverse transcriptase (RNA-dependent DNA polymerase) removes the 3' blocker from a first 3' blocked primer (RNA-dependent DNA pyrophosphorolysis), and then extends the 3' unblocked primer to generate a DNA product (RNA-dependent DNA polymerization). 2) Using the DNA product as template, a DNA-dependent DNA polymerase removes the 3' blocker from a second 3' blocked primer (DNA-dependent DNA pyrophosphorolysis), and then extends the 3' unblocked primer (DNA-dependent DNA polymerization). The first step, including RNA-dependent DNA pyrophosphorolysis and reverse transcription, is considered as the efficiency limit of the two-step process.

The four mutant DNA polymerases (reverse transcriptases or RNA-dependent DNA polymerases) of Cpe-665Y, Cfe-665Y, Cis-665Y and Cpe-Del-420Y (SEQ ID NOS: 5-8) were tested for RNA-dependent DNA pyrophosphorolysis and reverse transcription in RT-PAP because they were found to increase greatly the RNA-dependent DNA pyrophosphorolysis activities to remove the 3' blockers due to the Phenylalanine to Tyrosine substitutions.

We designed four RT-PAP Assays III, IV, V and VI (Table 6) to amplify RNA templates. Each assay had a forward primer and a reverse primer for exponential amplification. RT-PAP Assay III amplifies a 63-bp ACTB mRNA template with primers ACTB(426)25D and ACTB(488)30U (3' blocked primer) (SEQ IN NO: 21 and 22). RT-PAP Assay IV amplifies a 147-bp ACTB mRNA template with primers ACTB(426)25D and ACTB(572)30U (3' blocked primer) (SEQ IN NO: 23 and 24). RT-PAP Assay V amplifies a 76-bp COVID-19 viral RNA template with 3' blocked primers COVID-19(28679)28D and COVID-19(28754)28U (SEQ IN NO: 25 and 26). RT-PAP Assay VI amplifies a 80-bp ACTB mRNA template with 3' blocked primers ACTB(434)28D and ACTB(512)27U (SEQ IN NO: 27 and 28). The reverse primers, blocked by dideoxynucleotides at the 3' ends, matched the RNA templates.

Unless stated otherwise, the reaction composition and thermocycling program are described in EXAMPLE 3.
Heat-Inactivation To test heat-inactivation in detail, we examined the effect of various temperatures on the mutant reverse transcriptases. A special program included gradient temperatures from 83° C. to 94° C. inserted before reverse transcription step.

With RT-PAP Assay III, after heated at 83° C. for 2 minutes, a little amplification signal (±), indicated by a much delayed Ct value and a much lower RFU (relative fluorescent unit), was observed, estimating that >90% of reverse transcriptase activity was inactivated (Right part of Table 7). With RT-PAP Assay IV, after heated at 83° C. for 2 minutes, no amplification signal was found. The difference is caused by their product sizes. With RT-PAP assays III and IV, at 85° C. or higher temperatures, no amplification signals were observed, estimating that >99% of reverse transcriptase activities were heat-inactivated (Right part of Table 7).

The reverse transcriptases showed similar levels of remaining reverse transcriptase activities although as low as 85% of identity among their amino acid sequences (Table 2) and as low as 90% of identity among their DNA polymerase A domains (Table 4).

Optimal Temperatures

To test optimal temperatures, we examined the effect of various reaction temperatures on the mutant reverse transcriptases. A special program entailed gradient temperatures from 56° C. to 66.5° C. for 10 minutes for reverse transcription step.

RT-PAP Assay IV is a larger and more difficult target for reverse transcription, and it reflects the optimal temperatures more clearly than RT-PAP Assay III.

With RT-PAP Assay IV, each mutant reverse transcriptase was used to measure Ct values at different temperatures (Right part of Table 8). Because Ct values are directly proportional to the reverse transcriptase activities or efficiencies, the Ct values can represent them. For comparison of the Ct values at different temperatures, a ΔCt is set which equals to a Ct value subtracts that at 60.1° C. (Right part of Table 8). The results showed that the reverse transcriptases catalyzed both RNA-dependent DNA pyrophosphorolysis and reverse transcription in the RT-PAP assays substantially from 56° C. to 66.5° C. (Left part of Table 8). At 60.1-62.7° C., the Ct values were earliest and the ΔCt values were the smallest, indicating the reverse transcriptase activities or efficiencies to be highest at 60.1-62.7° C.

In addition, other tests also showed that the reverse transcriptases still had observable activities at 55° C. and at 70° C.

The reverse transcriptases showed similar properties of the optimal temperatures even with as low as 85% of identity among their amino acid sequences (Table 2) and as low as 90% of identity among their DNA polymerase A domains (Table 4).

Specific Activity

In order to compare relative activities among the mutant reverse transcriptases, the specific activity is defined as the minimum amount (ng) of a reverse transcriptase that has an almost 100% efficiency in reverse transcription step.

RT-PAP Assay IV was chosen because it is a larger and more difficult target and measures the level of reverse transcriptase activity more clearly than RT-PAP Assay III.

We tested and compared the specific activities of the mutant reverse transcriptases. The amount of each reverse transcriptase was 2-fold serially diluted from up to 200 ng to 1 ng in 20 μl of reaction. The Ct value was determined to estimate its minimum amount of the reverse transcriptase with an almost 100% efficiency of reverse transcription (Right part of Table 9). For comparison of the relative activities among the reverse transcriptases, the ratio of the minimum amount of a reverse transcriptase to that of Cpe-665Y was counted (Right part of Table 9). The mutant reverse transcriptases showed various specific activities with Cpe-665Y DNA polymerase having the highest specific activity among them.

In melting curve analysis, only one melting peak showed the $T_m$ value to be 86° C. of the amplified product in RT-PAP Assay IV. No-template-control did not show any measurable Ct, showing specificity of the amplification.

In addition, when RT-PAP Assay III was used, the specific activities were higher with less amounts of the mutant reverse transcriptases required than those in RT-PAP Assay IV.

The reverse transcriptases showed various specific activities within a limited range, depending not only on the particular reverse transcriptases but also on the particular assays.

RT-PAP Assays for Detection of COVID-19 Viral RNA

RT-PAP assays were developed to detect COVID-19 viral RNA for clinical diagnostics.

Specifically, we used RT-PAP assay V to amplify a RNA target in the N region of the COVID-19 viral genome in a first tube with two blocked primers of COVID-19(28679) 28D and COVID-19(28754)28U (SEQ ID NOS: 25 and 26). The RT-PAP assay V includes two steps of RT and PAP. 1) Using the COVID-19 viral RNA template, a reverse transcriptase (Cpe-665Y) removes the 3' blocker from the 3' blocked primer [COVID-19(28754)28U, SEQ ID NO: 26], and then extends the 3' unblocked primer to generate a DNA product. 2) Using the DNA product as template, a DNA-dependent DNA polymerase (TaqFS) removes the 3' blockers from the 3' blocked primers [COVID-19(28679)28D and COVID-19(28754)28U, SEQ ID NOS: 25 and 26]. The amplified product was measured by real-time fluorescence signals emitted by SYBR Green (EXAMPLE 3).

The sensitivity of RT-PAP assay V was validated. In an experiment, the amount of COVID-19 RNA template was 10-fold serially diluted with detection limit estimated to be a single digit of copies of RNA template (FIG. 1).

In addition, we used RT-PAP assay VI to amplify a control RNA of the human ACTB gene in a second tube with two blocked primers of ACTB(434)28D and ACTB(512)27U (SEQ ID NOS: 27 and 28).

Figure 2:
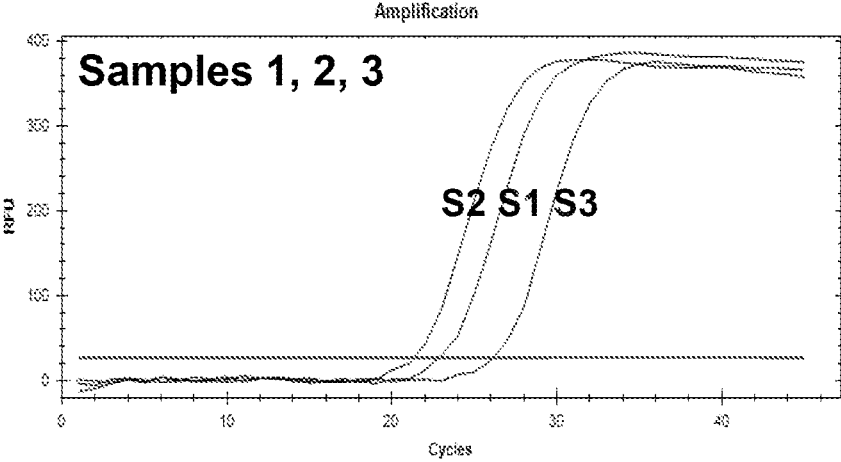
FIG. 2 shows applications of RT-PAP assays V and VI to clinical diagnostics. RT-PAP assay V is used to amplify a potential COVID-19 viral RNA template (Panels A, B and C). RT-PAP assay VI is used to amplify a potential control RNA template of the human ACTB gene (Panels D, E and F). Three COVID-19 positive RNA samples (S1 to S3), three COVID-19 negative RNA samples (S4 to S6), and three non-template controls were exampled. In addition, in melting curve analysis, the amplified products showed correct $T_m$ values (Tm=81° C. with amplified COVID-19 products, and $T_m$=81° C. with amplified ACTB products).
Figure 2:
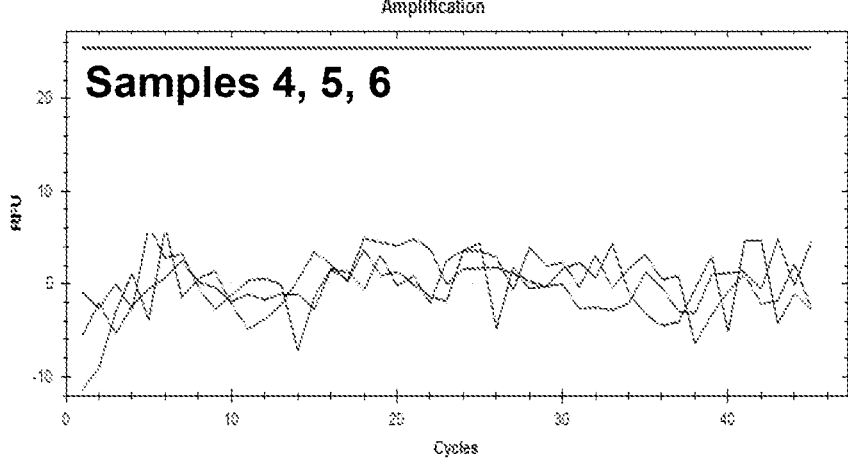
Figure 2:
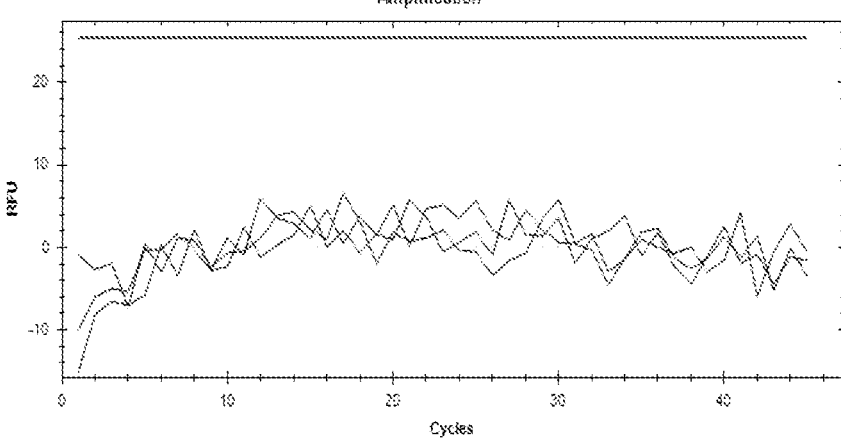
Figure 2:
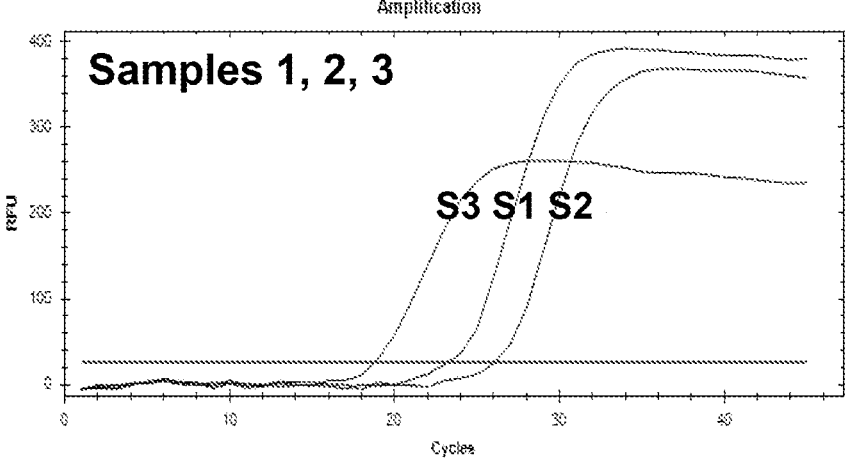
Figure 2:
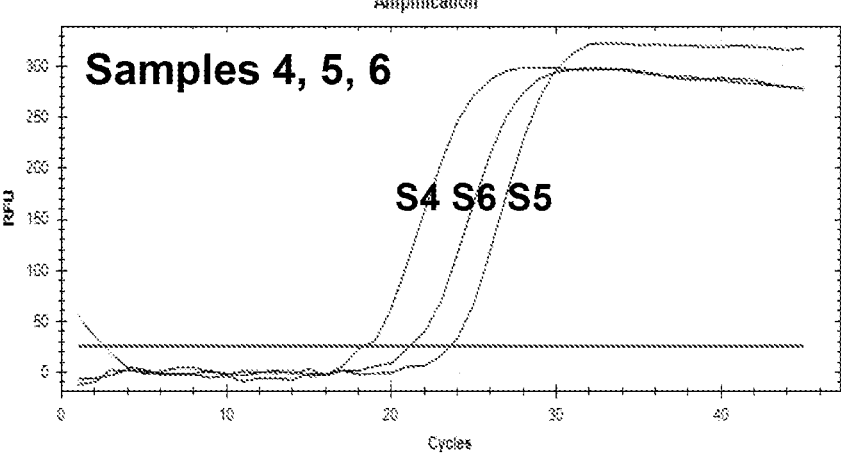
Figure 2:
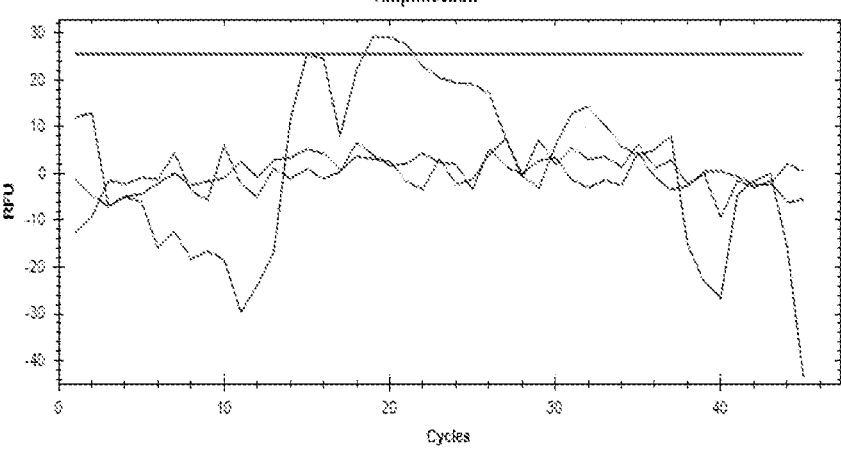

The application to clinical samples was demonstrated for RT-PAP Assay V to amplify a potential COVID-19 viral RNA template and for RT-PAP Assay VI to amplify a control RNA template of the human ACTB gene. COVID-19 positive, negative and non-template-control samples were tested and showed true positive and true negative results. In addition, no false positives and no false negatives were observed (FIG. 2).

Example 6

Other compositions and their concentrations, such as reaction buffer compositions and their concentrations, Magnesium concentrations and dNTP concentrations, were optimized together with the cycling programs, as described in EXAMPLE 3.

REFERENCE

Arion, D., Kaushik, N., McCormick, S., Borkow, G., and Parniak, M. A. (1998). Phenotypic mechanism of HIV-1 resistance to 3'-azido-3'-deoxythymidine (AZT): increased polymerization processivity and enhanced sensitivity to pyrophosphate of the mutant viral reverse transcriptase. Biochemistry 37, 15908-15917.

Ausubel, F. M. (1994). Current protocols in molecular biology, John Wiley & Sons, New York Deutscher, M. P., and Kornberg, A. (1969). Enzymatic synthesis of deoxyribonucleic acid. 28. The pyrophosphate exchange and pyrophosphorolysis reactions of deoxyribonucleic acid polymerase. The Journal of biological chemistry 244, 3019-3028.

Gardner, A. F., Joyce, C. M., and Jack, W. E. (2004). Comparative kinetics of nucleotide analog incorporation by vent DNA polymerase. The Journal of biological chemistry 279, 11834-11842.

Jones, M. D., and Foulkes, N. S. (1989). Reverse transcription of mRNA by Thermus aquaticus DNA polymerase. Nucleic acids research 17, 8387-8388.

Myers, T. W., and Gelfand, D. H. (1991). Reverse transcription and DNA amplification by a Thermus thermophilus DNA polymerase. Biochemistry 30, 7661-7666.

Liu, Q., and Sommer, S. S. (2000). Pyrophosphorolysis-activated polymerization (PAP): application to allele-specific amplification. BioTechniques 29, 1072-1080.

Liu, Q., and Sommer, S. S. (2002). Pyrophosphorolysis-activatable oligonucleotides may facilitate detection of rare alleles, mutation scanning and analysis of chromatin structures. Nucleic acids research 30, 598-604.

Liu, Q., and Sommer, S. S. (2004a). Pyrophosphorolysis by Type II DNA polymerases: implications for pyrophosphorolysis-activated polymerization. Analytical biochemistry 324, 22-28.

Liu, Q., and Sommer, S. S. (2004b). Detection of extremely rare alleles by bidirectional pyrophosphorolysis-activated polymerization allele-specific amplification (Bi-PAP-A): measurement of mutation load in mammalian tissues. BioTechniques 36, 156-166.

Sambrook, J., Fritsch, E. F., and Maniatis, T. (1989). Molecular cloning, a laboratory manual, second edition, Cold Spring Harbor Laboratory Press, Cold Spring Harbor, New York Sambrook, J., and Russell, D. W. (2001). Molecular Cloning: A Laboratory Manual, Third Edition, Cold Spring Harbor Laboratory Press, Cold Spring Harbor, New York.

Smith, E. S. E., Elfstrom, C. M., Gelfand, D. H., Higuchi, R. G., Myers, T. W., Schonbrunner, N. J., and Wang, A. M. (2007). High temperature reverse transcription using mutant DNA polymerases. U.S. Pat. No. 7,179,590.

Verma, I. M. (1977). The reverse transcriptase. Biochimica et biophysica acta 473, 1-38.

Urban, S., Fischer, K. P., and Tyrrell, D. L. (2001). Efficient pyrophosphorolysis by a hepatitis B virus polymerase may be a primer-unblocking mechanism. Proceedings of the National Academy of Sciences of the United States of America 98, 4984-4989.

The invention claimed is:

1. A method for reverse transcription using RNA-dependent DNA polymerization comprising: (a) providing a thermophilic purified DNA-dependent DNA polymerase of *Carboxydothermus pertinax* that catalyzes reverse transcription by RNA-dependent DNA polymerization on an RNA template, wherein the polymerase is also a reverse transcriptase and an RNA-dependent DNA polymerase comprising an amino acid sequence that has more than 95% sequence identity to DNA-dependent DNA polymerase of SEQ ID NO: 8; (b) catalyzing reverse transcription on an RNA template with the reverse transcriptase to generate a reverse-transcribed DNA; and then, (c) heat-inactivating the reverse transcriptase activity ≥83° C.; wherein the reverse transcriptase is >90% inactivated after 2 minutes at 83° C.

2. The method for reverse transcription of claim 1, wherein the reverse transcriptase comprises a DNA polymerase A domain that has an amino acid sequence with more than 95% sequence identity to DNA polymerase A domain of SEQ ID NO: 8, and wherein the reverse transcriptase activity is heat-inactivated.

3. The method for reverse transcription of claim 1, wherein step of heat inactivating the reverse transcriptase is carried out at a temperature from 83° C. to 95° C.

4. The method for reverse transcription of claim 1, wherein the step of reverse transcription is performed at a temperature from 55° C. to 70° C.

5. The method for reverse transcription of claim 1, wherein the reverse transcriptase has an optimal temperature from 60° C. to 62° C. for catalyzing reverse transcription.

6. The method for reverse transcription of claim 1, wherein the method further comprises (d) using a second DNA-dependent DNA polymerase to catalyze DNA-dependent DNA polymerization using the reverse-transcribed DNA as template.

7. The method for reverse transcription of claim 1, wherein the reverse transcriptase contains a tyrosine to phenylalanine substitution corresponding to position 420 of SEQ ID NO: 8.

8. A method for RNA-dependent DNA pyrophosphorolysis comprising:

(a) providing a thermophilic purified DNA-dependent DNA polymerase that catalyzes RNA-dependent DNA pyrophosphorolysis on an RNA template, wherein the polymerase is also a reverse transcriptase and an RNA-dependent DNA polymerase comprising an amino acid sequence that has more than 85% sequence identity to DNA-dependent DNA polymerase of SEQ ID NO: 8;

(b) providing a 3' blocked primer that has a non-extendable nucleotide at the 3'-blocker to anneal to an RNA template; and (c) catalyzing RNA-dependent DNA pyrophosphorolysis with the reverse transcriptase to remove the 3' blocker from the 3' blocked primer.

9. The method for RNA-dependent DNA pyrophosphorolysis of claim 8, wherein the reverse transcriptase comprises a DNA polymerase A domain that has an amino acid sequence with more than 90% sequence identity to DNA polymerase A domain of SEQ ID NO: 8.

10. The method for RNA-dependent DNA pyrophosphorolysis of claim 8, wherein the reverse transcriptase contains a phenylalanine to tyrosine substitution at amino acid position 420 of SEQ ID NO: 8.

11. The method for RNA-dependent DNA pyrophosphorolysis of claim 8, wherein the method further comprises steps (d): catalyzing reverse transcription on the RNA template with the reverse transcriptase to generate a reverse-transcribed DNA, and then (e) heat-inactivating the reverse transcriptase activity.

12. The method for RNA-dependent DNA pyrophosphorolysis of claim 8, wherein the step of heat inactivating the reverse transcriptase activity is carried out at a temperature >83° C.

13. The method for RNA-dependent DNA pyrophosphorolysis of claim 8, wherein the step of heat inactivating the reverse transcriptase is carried out at a temperature from 83° C. to 95° C.

14. The method for RNA-dependent DNA pyrophosphorolysis of claim 8, wherein the step of RNA-dependent DNA pyrophosphorolysis is carried out at a temperature from 55° C. to 70° C.

15. The method for RNA-dependent DNA pyrophosphorolysis of claim 8, wherein the reverse transcriptase has an optimal temperature from 60° C. to 62° C. for catalyzing RNA-dependent DNA pyrophosphorolysis.

16. The method for RNA-dependent DNA pyrophosphorolysis of claim 11, wherein the method further comprises:

(f) a second 3' blocked primer that has a non-extendable nucleotide at the 3' blocker anneals to the reverse-transcribed DNA template;

(g) a second DNA-dependent DNA polymerase that catalyzes DNA-dependent DNA pyrophosphorolysis to remove the 3' blocker from the 3' blocked primer to activate the primer; and (h) the second DNA-dependent DNA polymerase that catalyzes DNA-dependent DNA polymerization using the reverse-transcribed DNA as template.

17. The method for RNA-dependent DNA pyrophosphorolysis of claim 16 wherein the steps (a) to (h) are conducted in a single reaction tube.

* * * * *